(12) United States Patent
Rhonemus et al.

(10) Patent No.: US 11,214,589 B2
(45) Date of Patent: Jan. 4, 2022

(54) CRYSTALLINE FORMS OF NICOTINOYL RIBOSIDES AND DERIVATIVES THEREOF, AND METHODS OF PREPARATION THEREOF

(71) Applicant: ChromaDex Inc., Irvine, CA (US)

(72) Inventors: Troy Rhonemus, Mission Viejo, CA (US); Aron Erickson, Longmont, CO (US); Amanda Storjohann, Westminster, CO (US); Joshua Holloway, Longmont, CO (US); Philip Redpath, Portadown (GB)

(73) Assignee: ChromaDex Inc., Irvine, CA (US)

( * ) Notice: Subject to any disclaimer, the term of this patent is extended or adjusted under 35 U.S.C. 154(b) by 250 days.

(21) Appl. No.: 16/709,060

(22) Filed: Dec. 10, 2019

(65) Prior Publication Data

US 2020/0181188 A1 Jun. 11, 2020

Related U.S. Application Data

(60) Provisional application No. 62/777,567, filed on Dec. 10, 2018.

(51) Int. Cl.
*A01N 43/04* (2006.01)
*A61K 31/70* (2006.01)
*C07H 19/048* (2006.01)

(52) U.S. Cl.
CPC ........ *C07H 19/048* (2013.01); *C07B 2200/13* (2013.01)

(58) Field of Classification Search
None
See application file for complete search history.

(56) References Cited

U.S. PATENT DOCUMENTS 9,975,915 B1 5/2018 Migaud et al.
2018/0134743 A1 5/2018 Migaud et al.

FOREIGN PATENT DOCUMENTS

WO 2016014927 A2 1/2016
WO 2016144660 A1 9/2016

*Primary Examiner* — Patrick T Lewis
(74) *Attorney, Agent, or Firm* — Amin Talati Wasserman LLP; George M. Carrera, Jr.; Jonathan J. Krit

(57) ABSTRACT

The present disclosure provides crystalline Form II of nicotinic acid riboside, crystalline Form II of nicotinic acid riboside triacetate, and methods of preparation thereof.

32 Claims, 6 Drawing Sheets

CRYSTALLINE FORMS OF NICOTINOYL RIBOSIDES AND DERIVATIVES THEREOF, AND METHODS OF PREPARATION THEREOF

This application claims the benefit of U.S. Provisional application No. 62/777,567 filed on Dec. 10, 2018, which is hereby incorporated by reference herein in its entirety.

TECHNICAL FIELD

The present disclosure relates to nicotinoyl ribosides and reduced nicotinoyl ribosides, modified derivatives thereof, phosphorylated analogs thereof, and adenylyl dinucleotide conjugates thereof, crystalline forms thereof, and synthetic processes for the preparation thereof, the synthetic processes comprising processing of reagents by solvent-based processes, liquid-assisted mixing, milling, grinding, solvent-assisted grinding, extrusion, and/or recrystallization.

BACKGROUND

Vitamin B3, and other B-vitamins such as thiamine (vitamin B1), riboflavin (vitamin B2), and pyridoxine (vitamin B6) are extracted in their coenzyme forms from foodstuffs. During digestion, the coenzymes are catabolized to the free circulating vitamins, which are then passively or actively transported across membranes, and salvaged intracellularly to their respective cofactors. Mammals are entirely reliant on a dietary source of vitamin B1 and heavily dependent on the dietary supply of vitamins B2, B3, and B6. Of note, acute deficiencies in vitamin B1 and vitamin B3 affect identical organs, with identical outcomes if left untreated: dementia and death. Conditions such as diabetes and obesity, alcoholism, a high fat diet, and conditions where therapy impacts nutrition can compromise suitable absorption of these vitamins.

The dietary vitamin B3, which encompasses nicotinamide ("Nam" or "NM"), nicotinic acid ("NA"), and nicotinamide riboside ("NR"), is a precursor to the coenzyme nicotinamide adenine dinucleotide ("NAD$^+$"), its phosphorylated parent ("NADP$^+$" or "NAD(P)$^+$"), and their respective reduced forms ("NADH" and "NADPH," respectively).

Eukaryotes can synthesize NAD$^+$ de novo via the kynurenine pathway from tryptophan. See W. A. Krehl et al., *Growth-retarding Effect of Corn in Nicotinic Acid-Low Rations and its Counteraction by Tryptophane*, 101 SCIENCE 489 (1945); Gunther Schutz & Philip Feigelson, *Purification and Properties of Rat Liver Tryptophan Oxygenase*, 247 J. BIOL. CHEM. 5327 (1972); each of which is incorporated by reference herein in its entirety. The kynurenine pathway is a de novo pathway that originates from tryptophan. Through the sequential enzymatic action of tryptophan 2,3-dioxygenase ("TDO"), indoleamine 2,3-dioxygenase ("IDO"), kynurenine formamidase ("KFase"), kynurenine 3-hydroxylase ("K3H"), kynureninase, and 3-hydroxyanthranylate 3,4-dioxygenase ("3HAO"), tryptophan ("Trp") is converted to quinolinic acid ("QA"). See Javed A. Khan et al., *Nicotinamide adenine dinucleotide metabolism as an attractive target for drug discovery*, 11 EXPERT OPIN. THER. TARGETS 695 (2007), incorporated by reference herein in its entirety. Quinolinic acid (QA) is converted to nicotinic acid mononucleotide ("NaMN") through the action of quinolinic phosphoribosyltransferase ("QAPRTase'). See Khan et al., 2007.

The de novo kynureninase pathway, which produces nicotinic acid mononucleotide (NaMN) from quinolinic (QA), feeds into the well-established Preiss-Handler pathway, in which nicotinic acid mononucleotide (NaMN) is an intermediate. The Preiss-Handler pathway is a salvage pathway that starts with the conversion of nicotinic acid (NA) to nicotinic acid mononucleotide (NaMN), catalyzed by the enzyme nicotinate phosphoribosyltransferase ("NAPRT" or "NAPRTase"). Nicotinic acid mononucleotide (NaMN) is then adenylylated to form nicotinic acid adenine dinucleotide ("NaAD"), catalyzed by the enzyme nicotinic acid/nicotinamide mononucleotide adenylyltransferase ("NMNAT"). Nicotinic acid adenine dinucleotide (NaAD) is in turn amidated to form nicotinamide adenine dinucleotide (NAD$^+$), catalyzed by the enzyme nicotinamide adenine dinucleotide synthetase ("NADS"). Nicotinamide (Nam or NM), which is a breakdown product of NAD$^+$, can be converted to nicotinic acid (NA), catalyzed by the enzyme nicotinamide deamidase ("NM deamidase"). See Jack Preiss & Philip Handler, *Biosynthesis of Diphosphopyridine Nucleotide*, 233 J. BIOL. CHEM. 493 (1958), incorporated by reference herein in its entirety. See also Khan et al., 2007.

Another salvage pathway can convert nicotinamide (Nam or NM), the breakdown product of nicotinamide adenine dinucleotide (NAD$^+$), into nicotinamide mononucleotide ("NMN"), by the action of the enzyme nicotinamide phosphoribosyltransferase ("NMPRT" or "NMPRTase"). Nicotinamide mononucleotide (NMN) can then be directly converted into nicotinamide adenine dinucleotide (NAD$^+$) by nicotinic acid/nicotinamide mononucleotide adenylyltransferase (NMNAT). Alternatively, nicotinamide (Nam or NM) can be deamidated to form nicotinic acid (NA), which can then enter the Preiss-Handler pathway. Analysis of genome sequences suggests that the above two salvage pathways are often mutually exclusive; many organisms contain either NM deamidase or NMPRTase. See Khan et al., 2007.

Nicotinamide riboside (NR) can also be used as a precursor for nicotinamide adenine dinucleotide (NAD$^+$) biosynthesis, and nicotinamide riboside kinase ("NRK") catalyzes the phosphorylation of nicotinamide riboside (NR) to produce nicotinamide mononucleotide (NMN). See Khan et al., 2007.

Notably, nicotinamide riboside (NR) has not been considered a precursor to nicotinamide adenine dinucleotide (NAD$^+$) via the Preiss-Handler salvage pathway, or via conversion into nicotinic acid mononucleotide (NaMN) or nicotinic acid adenine dinucleotide (NaAD) as intermediates. Instead, the biosynthetic pathway for nicotinic acid riboside (NAR) is known to proceed directly to nicotinic acid mononucleotide (NaMN), then nicotinic acid adenine dinucleotide (NaAD), and ultimately to form NAD$^+$.

Nicotinamide adenine dinucleotide (NAD$^+$) is an enzyme co-factor and the central reduction-oxidation coenzyme that is essential for the function of several enzymes related to reduction-oxidation reactions and cellular energy metabolism. See Peter Belenky et al., NAD$^+$ metabolism in health and disease, 32 TRENDS IN BIOCHEMICAL SCIS. 12 (2007); Katrina L. Bogan & Charles Brenner, *Nicotinic Acid, Nicotinamide, and Nicotinamide Riboside: A Molecular Evaluation of NAD$^+$Precursor Vitamins in Human Nutrition*, 28 ANNUAL REV. OF NUTRITION 115 (2008); each of which is incorporated by reference herein in its entirety. Nicotinamide adenine dinucleotide (NAD$^+$) functions as an electron carrier or hydride group acceptor in cell metabolism, forming reduced nicotinamide adenine dinucleotide (NADH), with concomitant oxidation of metabolites derived from carbohydrates, amino acids, and fats. See Bogan & Brenner, 2008. The NAD$^+$/NADH ratio controls the degree to which such reactions proceed in oxidative versus reductive directions. Whereas fuel oxidation reactions require NAD$^+$ as a hydride acceptor, the processes of gluconeogenesis, oxidative phosphorylation, ketogenesis, detoxification of reactive oxygen species, and lipogenesis require reduced co-factors, NADH and NADPH, to act as hydride donors.

In addition to its role as a coenzyme, $NAD^+$ is the consumed substrate, and thus activator, of enzymes such as: poly-ADP-ribose polymerases ("PARPs"); sirtuins, a family of protein deacetylases that have been implicated in metabolic function and extended lifespan in lower organisms; and cyclic ADP-ribose synthetases. See Laurent Mouchiroud et al., *The $NAD^+$/Sirtuin Pathway Modulates Longevity through Activation of Mitochondrial UPR and FOXO Signaling*, 154 CELL 430 (2013), incorporated by reference herein in its entirety. See also Belenky et al., 2006. The co-enzymatic activity of $NAD^+$, together with the tight regulation of its biosynthesis and bioavailability, makes it an important metabolic monitoring system that is clearly involved in the aging process.

Once converted intracellularly to $NAD(P)^+$ and $NAD(P)H$, vitamin B3 metabolites are used as co-substrates in multiple intracellular protein modification processes, which control numerous essential signaling events (e.g., adenosine diphosphate ribosylation and deacetylation), and as cofactors in over 400 redox enzymatic reactions, thus controlling metabolism. This is demonstrated by a range of metabolic endpoints, which include the deacylation of key regulatory metabolic enzymes, resulting in the restoration of mitochondrial activity and oxygen consumption. Critically, mitochondrial dysfunction and cellular impairment have been correlated to the depletion of the NAD(P)(H)-cofactor pool, when the NAD(P)(H)-cofactor pool is present in sub-optimal intracellular concentrations. Vitamin B3 deficiency yields to evidenced compromised cellular activity through $NAD(P)^+$ depletion, and the beneficial effect of additional $NAD(P)^+$ bioavailability through NA, Nam, NR, and nicotinamide mononucleotide ("NMN") supplementation is primarily observed in cells and tissues where metabolism and mitochondrial function have been compromised.

In reduction-oxidation reactions, the nucleotide structures of $NAD^+$, NADH, $NADP^+$, and NADPH are preserved. In contrast, PARP, sirtuin, and cyclic ADP-ribose synthetase activities hydrolyze the glycosidic linkage between the nicotinamide (Nam or NM) and the ADP-ribosyl moieties of $NAD^+$ to signal DNA damage, alter gene expression, control post-translational modifications, and regulate calcium signaling.

In animals, $NAD^+$-consuming activities and cell division necessitate ongoing $NAD^+$ synthesis, either through the de novo pathway that originates with tryptophan, or via the salvage pathways from $NAD^+$-precursor vitamins nicotinamide (Nam or NM), nicotinic acid (NA), and nicotinamide riboside (NR). See Bogan & Brenner, 2008. Dietary $NAD^+$ precursors, which include tryptophan and the three $NAD^+$-precursor vitamins, prevent pellagra, a disease characterized by dermatitis, diarrhea, and dementia. The beneficial effect of additional $NAD^+$ bioavailability through nicotinamide (Nam or NM), nicotinic acid (NA), and nicotinamide riboside (NR) supplementation is primarily observed in cells and tissues where metabolism and mitochondrial function has been compromised.

Interestingly, supplementation with nicotinic acid (NA) and nicotinamide (Nam or NM), while critical in acute vitamin B3 deficiency, does not demonstrate the same physiological outcomes compared with that of nicotinamide riboside (NR) supplementation, even though, at the cellular level, all three metabolites are responsible for $NAD^+$ biosynthesis. This emphasizes the complexity of the pharmacokinetics and bio-distribution of B3-vitamin components. The bulk of intracellular $NAD^+$ is believed to be regenerated via the effective salvage of nicotinamide (Nam or NM), while de novo $NAD^+$ is obtained from tryptophan. See Anthony Rongvaux et al., *Reconstructing eukaryotic NAD metabolism*, 25 BIOESSAYS 683 (2003), incorporated by reference herein in its entirety. Crucially, these salvage and de novo pathways depend on the functional forms of vitamin B1, B2, and B6 to generate $NAD^+$ via a phosphoriboside pyrophosphate intermediate. Nicotinamide riboside (NR) is the only form of vitamin B3 from which $NAD^+$ can be generated in a manner independent of vitamin B1, B2, and B6, and the salvage pathway using NR for the production of $NAD^+$ is expressed in most eukaryotes.

Thiamine (vitamin B1), riboflavin (vitamin B2), niacin (vitamin B3), and pyridoxine (vitamin B6) are salvaged from food and converted back intracellularly to their respective, bioactive forms: Thiamine DiPhosphate ("ThDP"); Flavin Adenine Dinucleotide ("FAD"); Nicotinamide Adenine Dinucleotide ($NAD^+$); and PyridoxaL Phosphate ("PLP"). The conversion of vitamins B1, B2, and B6 to ThDP, FAD, and PLP, respectively, is ATP-dependent. Two of the three salvage pathways that convert vitamin B3 to $NAD^+$ are dependent on ThDP (B1), with the de novo production of $NAD^+$ from tryptophan depending on the bioactive forms of vitamins B1, B2, and B6. The vitamin B1 dependency comes from the fact that ThDP (B1) is cofactor for the transketolases involved in the biosynthesis of phosphoriboside pyrophosphate, an essential substrate in these aforementioned $NAD^+$ salvage and de novo pathways. The most recently identified, yet so far believed redundant, third $NAD^+$ salvage pathway, the Nicotinamide Riboside (NR) dependent $NAD^+$ biosynthetic pathway, does not require phosphoriboside pyrophosphate and is independent of vitamins B1, B2, and B6.

Though nicotinamide riboside (NR) is present in milk, the cellular concentrations of $NAD^+$, NADH, $NADP^+$, and NADPH are much higher than those of any other $NAD^+$ metabolites, such that dietary $NAD^+$ precursor vitamins are largely derived from enzymatic breakdown of $NAD^+$. See Pawel Bieganowski & Charles Brenner, *Discoveries of Nicotinamide Riboside as a Nutrient and Conserved NRK Genes Establish a Preiss-Handler Independent Route to $NAD^+$ in Fungi and Humans*, 117 CELL 495 (2002); Charles Evans et al., $NAD^+$ metabolite levels as a function of vitamins and calorie restriction: evidence for different mechanisms of longevity, 10 BMC CHEM. BIOL. 2 (2010); Samuel A. J. Trammell & Charles Brenner, *Targeted, LCMS-Based Metabolomics for Quantitative Measurement of $NAD^+$ Metabolites*, 4 COMPUTATIONAL & STRUCTURAL BIOTECH. J. 1 (2013); each of which is incorporated by reference herein in its entirety. Put another way, though milk is a source of nicotinamide riboside (NR), the more abundant sources of nicotinamide riboside (NR), nicotinamide (Nam or NM), and nicotinic acid (NA) are any whole foodstuffs in which cellular $NAD^+$ is broken down to these compounds. Human digestion and the microbiome play roles in the provision of these vitamins in ways that are not fully characterized.

Different tissues maintain $NAD^+$ levels through reliance of different biosynthetic routes. See Federica Zamporlini et al., *Novel assay for simultaneous measurement of pyridine mononucleotides synthesizing activities allows dissection of the $NAD^+$ biosynthetic machinery in mammalian cells*, 281 FEBS J. 5104 (2014); Valerio Mori et al., *Metabolic Profiling of Alternative NAD Biosynthetic Routes in Mouse Tissues*, 9 PLOS ONE e113939 (2014); each of which is incorporated by reference herein in its entirety. Because NAD$^+$-consuming activities frequently occur as a function of cellular stresses and produce nicotinamide (Nam or NM), the ability of a cell to salvage nicotinamide (Nam or NM) into productive NAD$^+$ synthesis through nicotinamide phosphoribosyltransferase ("NAMPT") activity versus methylation of nicotinamide (Nam or NM) to N-methylnicotinamide ("MeNam") regulates the efficiency of NAD$^+$-dependent processes. See Charles Brenner, *Metabolism. Targeting a fat-accumulation gene*, 508 NATURE 194 (2014); Veronique J. Bouchard et al., *PARP-1, a determinant of cell survival in response to DNA damage*, 31 EXPERIMENTAL HEMATOLOGY 446 (2003); each of which is incorporated by reference herein in its entirety. NAD$^+$ biosynthetic genes are also under circadian control, and both NAMPT expression and NAD$^+$ levels are reported to decline in a number of tissues as a function of aging and overnutrition. See Kathryn Moynihan Ramsey et al., *Circadian Clock Feedback Cycle Through NAMPT-Mediated NAD$^+$Biosynthesis*, 324 SCIENCE 651 (2009); Yasukazu Nakahata et al., *Circadian Control of the NAD$^+$Salvage Pathway by CLOCK-SIRT1*, 324 SCIENCE 654 (2009); Jun Yoshino et al., *Nicotinamide Mononucleotide, a Key NAD$^+$Intermediate Treats the Pathophysiology of Diet-and Age-Induced Diabetes in Mice*, 14 CELL METABOLISM 528 (2011); Ana P. Gomes et al., *Declining NAD$^+$ Induces a Pseudohypoxic State Disrupting Nuclear-Mitochondrial Communication during Aging*, 155 CELL 1624 (2013); Nady Braidy et al., *Mapping NAD$^+$metabolism in the brain of ageing Wistar rats: potential targets for influencing brain senescence*, 15 BIOGERONTOLOGY 177 (2014); Eric Verdin, *NAD$^+$ in aging, metabolism, and neurodegeneration*, 350 SCIENCE 1208 (2015); each of which is incorporated by reference herein in its entirety.

High-dose nicotinic acid (NA), but not high-dose nicotinamide (Nam or NM), has been used by people for decades to treat and prevent dyslipidemias, though its use is limited by painful flushing. See Joseph R. DiPalma & William S. Thayer, *Use of Niacin as a Drug*, 11 ANNUAL REV. OF NUTRITION 169 (1991); Jeffrey T. Kuvin et al., *Effects of Extended-Release Niacin on Lipoprotein Particle Size, Distribution, and Inflammatory Markers in Patients With Coronary Artery Disease*, 98 AM. J. OF CARDIOLOGY 743 (2006); each of which is incorporated by reference herein in its entirety. Though only approximately 15 milligrams per day of either nicotinic acid (NA) or nicotinamide (Nam or NM) is required to prevent pellagra, therapeutic doses of nicotinic acid (NA) can be as high as 2-4 grams. Despite the >100-fold difference in effective dose between pellagra prevention and treatment of dyslipidemias, the beneficial effects of nicotinic acid (NA) on plasma lipids depend on function of nicotinic acid (NA) as an NAD$^+$-boosting compound. See Belenky et al., 2007. According to this view, sirtuin activation would likely be part of the mechanism because nicotinamide (Nam or NM) is an NAD$^+$ precursor in most cells but is a sirtuin inhibitor at high doses. See Kevin J. Bitterman et al., *Inhibition of Silencing and Accelerated Aging by Nicotinamide, a Putative Negative Regulator of Yeast Sir2 and Human SIRT1*, 277 J. BIOL. CHEM. 45099 (2002), incorporated by reference herein in its entirety. See also Zamporlini et al., 2014; Mori et al., 2014.

NAD$^+$ was initially characterized as a co-enzyme for oxidoreductases. Though conversions between NAD$^+$, NADH, NADP$^+$, and NADPH would not be accompanied by a loss of total co-enzyme, it was discovered that NAD$^+$ is also turned over in cells for unknown purposes. See Morelly L. Maayan, *NAD$^+$-Glycohydrolase of Thyroid Homogenates*, 2014 NATURE 1169 (1964), incorporated by reference herein in its entirety. Sirtuin enzymes such as Sir2 of *S. cerevisiae* and its homologs deacetylate lysine residues with consumption of an equivalent of NAD$^+$, and this activity is required for Sir2 function as a transcriptional silencer. See S. Imai et al., *Sir2: An NAD-dependent Histone Deacetylase That Connects Chromatin Silencing, Metabolism, and Aging*, 65 COLD SPRING HARBOR SYMPOSIA ON QUANTITATIVE BIOLOGY 297 (2000), incorporated by reference herein in its entirety. NAD$^+$-dependent deacetylation reactions are required, not only for alterations in gene expression, but also for repression of ribosomal DNA recombination and extension of lifespan in response to calorie restriction. See Lin et al., *Requirement of NAD and SIR2 for Life-Span Extension by Calorie Restriction in Saccharomyces cerevisiae*, 289 SCIENCE 2126 (2000); Lin et al., *Calorie restriction extends Saccharomyces cerevisiae lifespan by increasing respiration*, 418 NATURE 344 (2002); each of which is incorporated by reference herein in its entirety. NAD$^+$ is consumed by Sir2 to produce a mixture of 2'- and 3'-O-acetylated ADP-ribose plus nicotinamide (Nam or NM) and the deacetylated polypeptide. See Anthony A. Sauve et al., *Chemistry of Gene Silencing: the Mechanism of NAD$^+$-Dependent Deacetylation Reactions*, 40 BIOCHEMISTRY 15456 (2001), incorporated by reference herein in its entirety. Additional enzymes, including poly(ADP-ribose) polymerases ("PARPs") and cADP-ribose synthases are also NAD$^+$-dependent and produce nicotinamide (Nam or NM) and ADP-ribosyl products. See Mathias Ziegler, *New functions of a long-known molecule*, 267 FEBS J. 1550 (2000); Alexander Bürkle, *Physiology and pathophysiology of poly (ADP-ribosyl)ation*, 23 BIOESSAYS 795 (2001); each of which is incorporated by reference herein in its entirety.

The non-coenzymatic properties of NAD$^+$ have renewed interest in NAD$^+$ biosynthesis. Based on the ability of nicotinamide riboside (NR) to elevate NAD$^+$ synthesis, increase sirtuin activity, and extend lifespan in yeast, nicotinamide riboside (NR) has been employed in mice to elevate NAD$^+$ metabolism and improve health in models of metabolic stress. See Peter Belenky et al., *Nicotinamide Riboside Promotes Sir2 Silencing and Extends Lifespan via Nrk and Urh1/Pnp1/Meu1 Pathways to NAD$^+$*, 129 CELL 473 (2007), incorporated by reference herein in its entirety. See also Bieganowski & Brenner, 2004. Notably, nicotinamide riboside (NR) allowed mice to resist weight gain on a high-fat diet, and to prevent noise-induced hearing loss. See Carles Cantó et al., *The NAD$^+$Precursor Nicotinamide Riboside Enhances Oxidative Metabolism and Protects against High-Fat Diet-Induced Obesity*, 15 CELL METABOLISM 838 (2012); Kevin D. Brown et al., *Activation of SIRT3 by the NAD$^+$Precursor Nicotinamide Riboside Protects from Noise-Induced Hearing Loss*, 20 CELL METABOLISM 1059 (2014); each of which is incorporated by reference herein in its entirety. Data indicate that nicotinamide riboside (NR) is a mitochondrially favored NAD$^+$ precursor and, indeed, in vivo activities of nicotinamide riboside (NR) have been interpreted as depending upon mitochondrial sirtuin activities, though not to the exclusion of nucleocytosolic targets. Andrey Nikiforov et al., *Pathways and Subcellular Compartmentation of NAD Biosynthesis in Human Cells*, 286 J. BIOLOGICAL CHEM. 21767 (2011); Charles Brenner, *Boosting NAD to Spare Hearing*, 20 CELL METABOLISM 926 (2014); Carles Cantó et al., *NAD$^+$Metabolism and the Control of Energy Homeostasis: A Balancing Act between Mitochondria and the Nucleus*, 22 CELL METABOLISM 31 (2015); each of which is incorporated by reference herein in its entirety. Similarly, nicotinamide mononucleotide (NMN), the phosphorylated form of nicotinamide riboside (NR), has been used to treat declining NAD$^+$ in mouse models of overnutrition and aging. See J. Yoshino et al., 2011; A. P. Gomes et al., 2013. Because of the abundance of NAD$^+$-dependent processes, it is not known to what degree NAD$^+$-boosting strategies are mechanistically dependent upon particular molecules such as SIRT1 or SIRT3. In addition, the quantitative effect of nicotinamide riboside (NR) on the NAD$^+$ metabolome has not been reported in any system.

In conclusion, vitamins B1, B2, B3, and B6 are closely intertwined in their biosynthetic pathways, with the maintenance and regeneration of the NADPH intracellular pool depending on the availability of ThDP (vitamin B1), FAD (vitamin B2), and PLP (vitamin B6), along with that of ATP. Critically, the latter is produced through NAD$^+$-dependent OXPHOS and glycolysis, and is necessary for the functionalization of the vitamins B1, B2, and B6 to ThDP, FAD, and PLP, respectively. A shortage of any of these vitamins would impact negatively on the biology of the others. Maximizing these vitamins' bioavailabilities is achieved by conjugating these vitamins to NR, NAR, NRH, or NARH, or their related derivatives, and by using the NR/NAR uptake to achieve improved vitamin bioavailability.

WO 2016/014927 A2, incorporated by reference herein in its entirety, describes crystalline forms of nicotinamide riboside, including a Form I of nicotinamide riboside chloride. Also disclosed are pharmaceutical compositions comprising the crystalline Form I of nicotinamide riboside chloride, and methods of producing such pharmaceutical compositions.

WO 2016/144660 A1, incorporated by reference herein in its entirety, describes crystalline forms of nicotinamide riboside, including a Form II of nicotinamide riboside chloride. Also disclosed are pharmaceutical compositions comprising the crystalline Form II of nicotinamide riboside chloride, and methods of producing such pharmaceutical compositions.

U.S. Pat. No. 9,975,915, incorporated by reference herein in its entirety, describes crystalline forms of nicotinamide riboside, including a NR methanolate Form II of nicotinamide riboside chloride. Also disclosed are compositions comprising the NR methanolate Form II of nicotinamide riboside chloride, and methods of preparation of the NR methanolate Form II of nicotinamide riboside chloride. Also disclosed are crystalline forms of nicotinic acid riboside (NAR), including a Form I of nicotinic acid riboside (NAR). Also disclosed are compositions comprising the Form I of nicotinic acid riboside (NAR), and methods of preparation of the Form I of nicotinic acid riboside (NAR). Also disclosed are crystalline forms of nicotinamide riboside triacetate (1-(2',3',5'-triacetyl-beta-D-ribofuranosyl)-nicotinamide, "NR triacetate," or "NRTA"), including a Form I of nicotinamide riboside triacetate (NRTA). Also disclosed are compositions comprising the Form I of nicotinamide riboside triacetate (NRTA), and methods of preparation of the Form I of nicotinamide riboside triacetate (NRTA). Also disclosed are crystalline forms of nicotinic acid riboside triacetate (1-(2',3',5'-triacetyl-beta-D-ribofuranosyl)-nicotinic acid, "NAR triacetate," or "NARTA"), including a Form I of nicotinic acid riboside triacetate (NARTA). Also disclosed are compositions comprising the Form I of nicotinic acid riboside triacetate (NARTA), and methods of preparation of the Form I of nicotinic acid riboside triacetate (NARTA). Also disclosed are crystalline forms of nicotinamide mononucleotide ("NMN"), including a Form III of nicotinamide mononucleotide (NMN), and a Form IV of nicotinamide mononucleotide (NMN). Also disclosed are compositions comprising the Form III of nicotinamide mononucleotide (NMN) and compositions comprising the Form IV of nicotinamide mononucleotide (NMN), and methods of preparation of the Form III of nicotinamide mononucleotide (NMN) and methods of preparation of the Form IV of nicotinamide mononucleotide (NMN).

In view of the above, if new compounds and derivatives comprising nicotinoyl riboside conjugates, or derivatives thereof, or salts, hydrates, solvates, or prodrugs thereof, or crystal forms thereof, could be found, this would represent a useful contribution to the art. Furthermore, if new methods of preparing compounds and derivatives comprising nicotinoyl riboside conjugates, or derivatives thereof, or salts, hydrates, solvates, or prodrugs thereof, or crystal forms thereof, could be found, this would also represent a useful contribution to the art.

In view of the above, there is a need for processes that are atom-efficient in terms of reagent and solvent equivalency, that bypass the need for polar, non-GRAS ("generally recognized as safe") solvents, that are versatile in terms of limitations associated with solubility and reagent mixing, that are time- and energy-efficient, and that provide efficient, practical, and scalable methods for the preparation of nicotinoyl ribosides.

In view of the above, there is a need for novel derivatives and novel crystalline forms of nicotinoyl ribosides.

SUMMARY OF THE INVENTION

In an embodiment, the present disclosure relates to crystalline forms of nicotinoyl ribosides, derivatives thereof, or salts, hydrates, solvates, or prodrugs thereof.

In another embodiment, the present disclosure relates to synthetic sequences or processes that enable the efficient production of crystalline forms of nicotinoyl ribosides, derivatives thereof, or salts, hydrates, solvates, or prodrugs thereof.

In yet another embodiment, the present disclosure relates to scalable methods of preparation of crystalline forms of nicotinic acid riboside (NAR), and derivatives thereof, or salts, hydrates, solvates, or prodrugs thereof.

In yet another embodiment, the present disclosure relates to scalable methods of preparation of crystalline forms of nicotinic acid riboside triacetate ("NARTA"), and derivatives thereof, or salts, hydrates, solvates, or prodrugs thereof.

In yet another embodiment, the present disclosure relates to crystalline forms of nicotinic acid riboside (1-(beta-D-ribofuranosyl)-nicotinic acid, NAR), including, but not limited to, a "Form II" of nicotinic acid riboside (NAR), and methods of preparation thereof.

In yet another embodiment, the present disclosure relates to crystalline forms of nicotinic acid riboside triacetate (1-(2',3',5'-triacetyl-beta-D-ribofuranosyl)-nicotinic acid, "NAR triacetate," or "NARTA"), including, but not limited to, a "Form II" of nicotinic acid riboside triacetate (NARTA), and methods of preparation thereof.

In an embodiment, the present disclosure provides a novel crystalline Form II of nicotinic acid riboside (NAR), according to formula (I):

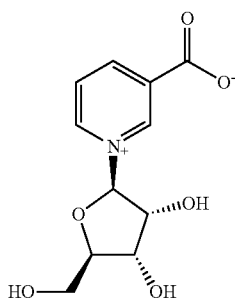

(I)

In another embodiment, the above crystalline Form II of nicotinic acid riboside (NAR) can be characterized by a powder X-ray diffraction pattern having peaks at 16.9, 17.7, and 26.6 degrees two theta±0.2 degrees two theta. In yet another embodiment, the above crystalline Form II of nicotinic acid riboside (NAR) can be characterized by a powder X-ray diffraction pattern having peaks at 8.5, 15.8, 16.9, 17.7, and 26.6 degrees two theta±0.2 degrees two theta. In yet another embodiment, the above crystalline Form II of nicotinic acid riboside (NAR) can be characterized by a powder X-ray diffraction pattern having peaks at 8.5, 13.9, 15.8, 16.9, 17.7, 21.7, 22.0, 26.1, 26.6, and 27.9 degrees two theta±0.2 degrees two theta. In yet another embodiment, the above crystalline Form II of nicotinic acid riboside (NAR) can be characterized by a powder X-ray diffraction pattern having peaks substantially as shown in FIG. 1. In yet another embodiment, the above crystalline Form II of nicotinic acid riboside (NAR) can be characterized by a powder X-ray diffraction pattern having peaks substantially as provided in Table 1±0.2 degrees two theta.

In yet another embodiment, the above crystalline Form II of nicotinic acid riboside (NAR) can be characterized by an IR spectrum having peaks at 754.0, 775.3, 867.8, 923.8, and 1641.2 $cm^{-1}±0.2$ $cm^{-1}$. In yet another embodiment, the above crystalline Form II of nicotinic acid riboside (NAR) can be characterized by an IR spectrum having peaks at 754.0, 775.3, 867.8, 923.8, 1054.9, 1087.7, 1114.7, 1135.9, 1184.1, and 1641.2 $cm^{-1}±0.2$ $cm^{-1}$. In yet another embodiment, the above crystalline Form II of nicotinic acid riboside (NAR) can be characterized by an IR spectrum having peaks 754.0, 775.3, 867.3, 867.8, 923.8, 1054.9, 1087.7, 1114.7, 1135.9, 1184.1, 1309.5, 1322.9, 1359.6, 1641.2 $cm^{-1}±0.2$ $cm^{-1}$. In yet another embodiment, the above crystalline Form II of nicotinic acid riboside (NAR) can be characterized by an IR spectrum having peaks 754.0, 775.3, 867.8, 923.8, 1054.9, 1087.7, 1114.7, 1135.9, 1114.7, 1135.9, 1184.1, 1309.5, 1322.9, 1359.6, 1579.4, 1612.2, 1641.2, 3043.2, and 3259.2 $cm^{-1}±0.2$ $cm^{-1}$. In yet another embodiment, the above crystalline Form II of nicotinic acid riboside (NAR) can be characterized by an IR spectrum substantially as shown in FIG. 2.

In yet another embodiment, the above crystalline Form II of nicotinic acid riboside (NAR) can be characterized by a DSC thermogram substantially as shown in FIG. 3. In yet another embodiment, the above crystalline Form II of nicotinic acid riboside (NAR) can be characterized by a DSC thermogram obtained using a heating rate of 10° C./min comprising an endothermic event with an onset temperature of 153.0° C.±2° C. In yet another embodiment, the above crystalline Form II of nicotinic acid riboside (NAR) can be characterized by a DSC thermogram obtained using a heating rate of 10° C./min comprising an endothermic event with a peak temperature of 155.9° C.±2° C. In yet another embodiment, the above crystalline Form II of nicotinic acid riboside (NAR) can be characterized by a DSC thermogram obtained using a heating rate of 10° C./min comprising an endothermic event with an onset temperature of 153.0° C.±2° C. and a peak temperature of 155.9° C.±2° C.

In an embodiment, the above crystalline Form II of nicotinic acid riboside (NAR) can be prepared by a method that can include the steps of:

(a) adding a volume of hexafluoroisopropanol to a mass of nicotinic acid riboside (NAR) such that the mass (mg) to volume (mL) ratio of nicotinic acid riboside (NAR) to hexafluoroisopropanol is about 36:1; (b) dissolving the mass of nicotinic acid riboside (NAR) in the volume of hexafluoroisopropanol so as to produce a solution of nicotinic acid riboside (NAR) in hexafluoroisopropanol; optionally, (b1) filtering the solution of nicotinic acid riboside (NAR) in hexafluoroisopropanol; (c) adding the solution of nicotinic acid riboside (NAR) in hexafluoroisopropanol to an open vessel; (d) placing the open vessel containing the solution of nicotinic acid riboside (NAR) in hexafluoroisopropanol inside a larger vessel containing a volume of ethyl acetate that is approximately equal to the volume of the solution of nicotinic acid riboside (NAR) in hexafluoroisopropanol; (e) sealing the larger vessel; (f) maintaining the solution of nicotinic acid riboside (NAR) in hexafluoroisopropanol at ambient temperature so as to crystallize the crystalline Form II of nicotinic acid riboside (NAR); optionally, (f1) unsealing the larger vessel; optionally, (f2) adding an additional volume of ethyl acetate to the larger vessel that is approximately half of the volume of ethyl acetate contained in the larger vessel according to step (d); optionally, (f3) maintaining the solution of nicotinic acid riboside (NAR) in hexafluoroisopropanol at ambient temperature for at least 7 days; (g) unsealing the larger vessel; (h) removing the open vessel from the larger vessel; and (i) isolating the crystalline Form II of nicotinic acid riboside (NAR).

The process described herein above effects a preparation of the above crystalline Form II of nicotinic acid riboside.

In another embodiment, the above crystalline Form II of nicotinic acid riboside (NAR) can be prepared by a method that can include the steps of:

(a) adding a volume of hexafluoroisopropanol to a mass of nicotinic acid riboside (NAR) such that the mass (mg) to volume (mL) ratio of nicotinic acid riboside (NAR) to hexafluoroisopropanol is about 36:1; (b) dissolving the mass of nicotinic acid riboside (NAR) in the volume of hexafluoroisopropanol so as to produce a solution of nicotinic acid riboside (NAR) in hexafluoroisopropanol; optionally, (b1) filtering the solution of nicotinic acid riboside (NAR) in hexafluoroisopropanol; (c) adding the solution of nicotinic acid riboside (NAR) in hexafluoroisopropanol to an open vessel; (d) placing the open vessel containing the solution of nicotinic acid riboside (NAR) in hexafluoroisopropanol inside a larger vessel containing a volume of ethyl acetate that is approximately equal to the volume of the solution of nicotinic acid riboside (NAR) in hexafluoroisopropanol; (e) sealing the larger vessel; (f) maintaining the solution of nicotinic acid riboside (NAR) in hexafluoroisopropanol at ambient temperature for at least 7 days so as to crystallize the crystalline Form II of nicotinic acid riboside (NAR); optionally, (f1) unsealing the larger vessel; optionally, (f2) adding an additional volume of ethyl acetate to the larger vessel that is approximately half of the volume of ethyl acetate contained in the larger vessel according to step (d); optionally, (f3) maintaining the solution of nicotinic acid riboside (NAR) in hexafluoroisopropanol at ambient temperature for at least 7 days; (g) unsealing the larger vessel; (h) removing the open vessel from the larger vessel; and (i) isolating the crystalline Form II of nicotinic acid riboside (NAR).

The process described herein above effects a preparation of the above crystalline Form II of nicotinic acid riboside.

In an embodiment, the present disclosure provides a novel crystalline Form II of nicotinic acid riboside triacetate (NARTA), according to formula (II):

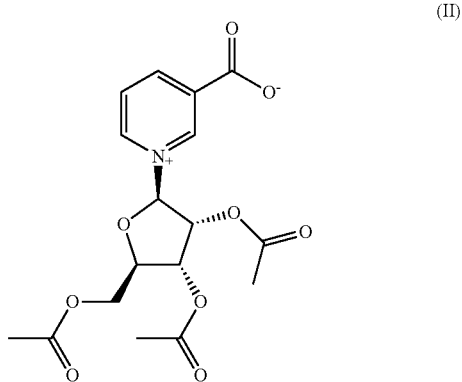 [SMILES: CC(=O)OC[C@H]1O[C@@H]([n+]2cccc(C(=O)[O-])c2)[C@H](OC(C)=O)[C@@H]1OC(C)=O]

In another embodiment, the above crystalline Form II of nicotinic acid riboside triacetate can be characterized by a powder X-ray diffraction pattern having peaks at 8.0, 9.7, and 19.4 degrees two theta±0.2 degrees two theta. In yet another embodiment, the above crystalline Form II of nicotinic acid riboside triacetate can be characterized by a powder X-ray diffraction pattern having peaks at 8.0, 9.7, 11.7, 19.0, 19.4, and 23.5 degrees two theta±0.2 degrees two theta. In yet another embodiment, the above crystalline Form II of nicotinic acid riboside triacetate can be characterized by a powder X-ray diffraction pattern having peaks at 8.0, 9.7, 11.7, 12.6, 14.7, 16.8, 19.0, 19.4, 22.4, 23.5, and 25.1 degrees two theta±0.2 degrees two theta. In yet another embodiment, the above crystalline Form II of nicotinic acid riboside triacetate can be characterized by a powder X-ray diffraction pattern having peaks substantially as shown in FIG. 4. In yet another embodiment, the above crystalline Form II of nicotinic acid riboside triacetate can be characterized by a powder X-ray diffraction pattern having peaks substantially as provided in Table 3±0.2 degrees two theta.

In yet another embodiment, the above crystalline Form II of nicotinic acid riboside triacetate can be characterized by an IR spectrum having peaks at 599.3, 659.6, 683.2, 694.3, 710.7, 770.0, 809.0, 856.7, 893.4, 922.8, 948.8, 1638.7, and 1738.5 $cm^{-1}\pm0.2\ cm^{-1}$. In yet another embodiment, the above crystalline Form II of nicotinic acid riboside triacetate can be characterized by an IR spectrum having peaks at 599.3, 659.6, 683.2, 694.3, 710.7, 770.0, 809.0, 856.7, 893.4, 922.8, 948.8, 1026.4, 1060.7, 1097.3, 1215.4, 1358.2, 1473.2, 1483.0, 1638.7, and 1738.5 $cm^{-1}\pm0.2\ cm^{-1}$. In yet another embodiment, the above crystalline Form II of nicotinic acid riboside triacetate can be characterized by an IR spectrum having peaks at 599.3, 659.6, 683.2, 694.3, 710.7, 770.0, 809.0, 856.7, 893.4, 922.8, 948.8, 1026.4, 1060.7, 1097.3, 1215.4, 1358.2, 1473.2, 1483.0, 1579.0, 1612.2, 1638.7, and 1738.5 $cm^{-1}\pm0.2\ cm^{-1}$. In yet another embodiment, the above crystalline Form II of nicotinic acid riboside triacetate can be characterized by an IR spectrum having peaks substantially as provided in Table 4±0.2 $cm^{-1}$. In yet another embodiment, the above crystalline Form II of nicotinic acid riboside triacetate can be characterized by an IR spectrum substantially as shown in FIG. 5.

In yet another embodiment, the above crystalline Form II of nicotinic acid riboside triacetate can be characterized by a DSC thermogram substantially as shown in FIG. 6. In yet another embodiment, the above crystalline Form II of nicotinic acid riboside triacetate can be characterized by a DSC thermogram obtained using a heating rate of 10° C./min comprising an endothermic event with an onset temperature of 92.2°±2° C. In yet another embodiment, the above crystalline Form II of nicotinic acid riboside triacetate can be characterized by a DSC thermogram obtained using a heating rate of 10° C./min comprising an endothermic event with an onset temperature of 159.2° C.±2° C. In yet another embodiment, the above crystalline Form II of nicotinic acid riboside triacetate can be characterized by a DSC thermogram obtained using a heating rate of 10° C./min comprising endothermic events with onset temperatures at 92.2° C.±2° C. and 159.2° C.±2° C.

In an embodiment, the above crystalline Form II of nicotinic acid riboside triacetate (NARTA) can be prepared by a method that can include the steps of:
(a) adding a volume of ethanol to a mass of nicotinic acid riboside triacetate (NARTA) in a vessel such that the mass (mg) to volume (mL) ratio of nicotinic acid riboside triacetate (NARTA) to ethanol is about 67:1; (b) dissolving the mass of nicotinic acid riboside triacetate (NARTA) in the volume of ethanol at approximately 50° C. so as to produce a solution of nicotinic acid riboside triacetate (NARTA) in ethanol; (c) cooling the solution of nicotinic acid riboside triacetate (NARTA) in ethanol at −20° C. so as to crystallize the crystalline Form II of nicotinic acid riboside triacetate (NARTA); and (d) isolating the crystalline Form II of nicotinic acid riboside triacetate (NARTA).

The process described herein effects a preparation of a crystalline Form II of nicotinic acid riboside triacetate (NARTA).

In another embodiment, the above crystalline Form II of nicotinic acid riboside triacetate (NARTA) can be prepared by a method that can include the steps of:
(a) adding a volume of ethanol to a mass of nicotinic acid riboside triacetate (NARTA) in a vessel such that the mass (mg) to volume (mL) ratio of nicotinic acid riboside triacetate (NARTA) to ethanol is about 67:1; (b) dissolving the mass of nicotinic acid riboside triacetate (NARTA) in the volume of ethanol at approximately 50° C. so as to produce a solution of nicotinic acid riboside triacetate (NARTA) in ethanol; (c) cooling the solution of nicotinic acid riboside triacetate (NARTA) in ethanol at −20° C. for at least 24 hours so as to crystallize the crystalline Form II of nicotinic acid riboside triacetate (NARTA); and (d) isolating the crystalline Form II of nicotinic acid riboside triacetate (NARTA).

The process described herein effects a preparation of a crystalline Form II of nicotinic acid riboside triacetate (NARTA).

DETAILED DESCRIPTION

Figure 1:
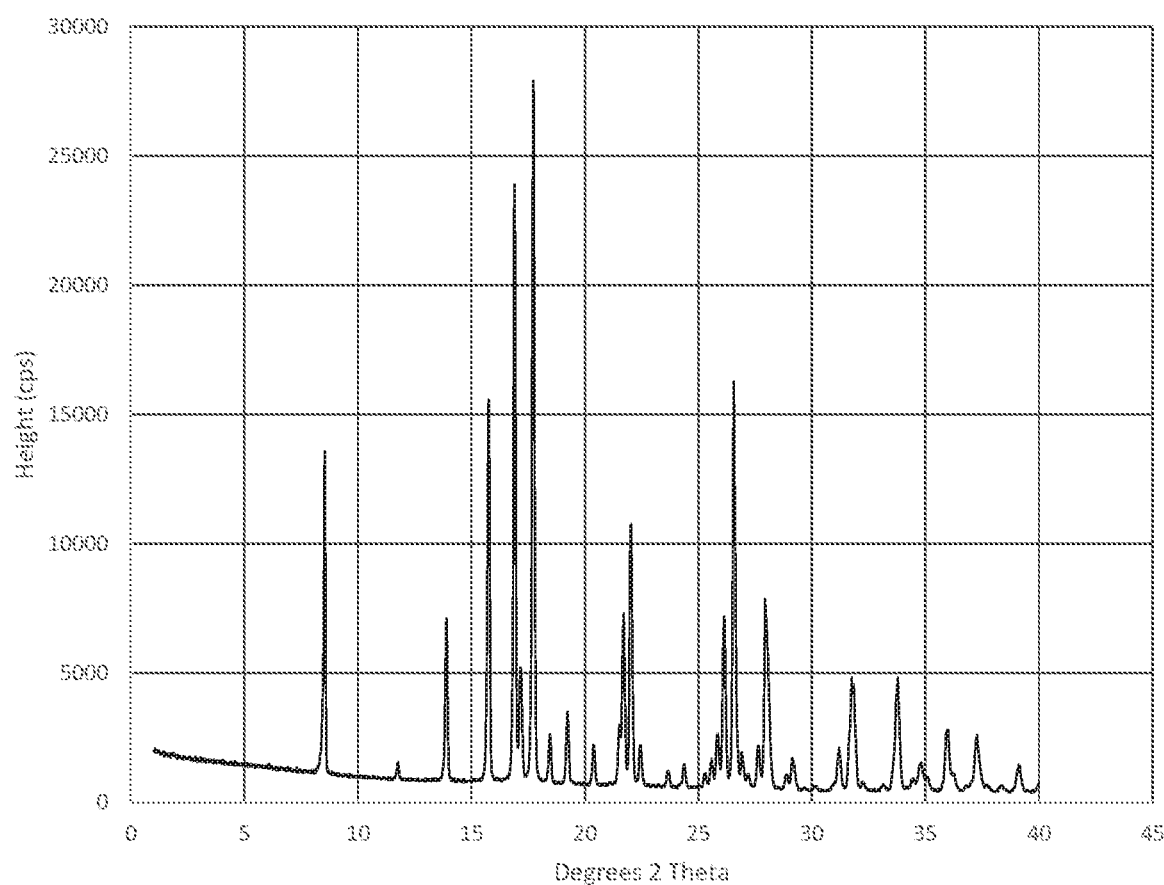
FIG. 1 provides an X-ray powder diffraction pattern for the presently disclosed Form II of crystalline nicotinic acid riboside (NAR), the compound having formula (I), prepared according to an embodiment of the presently disclosed methods for the preparation of a crystalline form of nicotinic acid riboside (NAR).

In an embodiment, the present disclosure relates to crystalline forms of nicotinoyl ribosides, derivatives thereof, or salts, hydrates, solvates, or prodrugs thereof.

In another embodiment, the present disclosure relates to synthetic sequences or processes that enable the efficient production of crystalline forms of nicotinoyl ribosides, derivatives thereof, or salts, hydrates, solvates, or prodrugs thereof.

In yet another embodiment, the present disclosure relates to scalable methods of preparation of crystalline forms of nicotinic acid riboside, and derivatives thereof, or salts, hydrates, solvates, or prodrugs thereof.

In yet another embodiment, the present disclosure relates to scalable methods of preparation of crystalline forms of nicotinic acid riboside triacetate ("NARTA"), and derivatives thereof, or salts, hydrates, solvates, or prodrugs thereof.

In yet another embodiment, the present disclosure relates to crystalline forms of nicotinic acid riboside (1-(beta-D-ribofuranosyl)-nicotinic acid, NAR), including, but not limited to, a "Form II" of nicotinic acid riboside (NAR), and methods of preparation thereof.

In yet another embodiment, the present disclosure relates to crystalline forms of nicotinic acid riboside triacetate (1-(2',3',5'-triacetyl-beta-D-ribofuranosyl)-nicotinic acid, "NAR triacetate," or "NARTA"), including, but not limited to, a "Form II" of nicotinic acid riboside triacetate (NARTA), and methods of preparation thereof.

In yet another embodiment, the present disclosure relates to crystalline forms of reduced nicotinamide riboside (NRH, IV), or salts, solvates, hydrates, or prodrugs thereof, and methods of preparation thereof.

In yet another embodiment, the present disclosure relates to crystalline forms of reduced nicotinic acid riboside (NARH, V), or salts, solvates, hydrates, or prodrugs thereof, and methods of preparation thereof.

In yet another embodiment, the present disclosure relates to crystalline forms of nicotinamide riboside triacetate (NRTA, VI), or salts, solvates, hydrates, or prodrugs thereof, and methods of preparation thereof.

In yet another embodiment, the present disclosure relates to crystalline forms of reduced nicotinamide riboside triacetate (NRH-TA, VII), or salts, solvates, hydrates, or prodrugs thereof, and methods of preparation thereof.

In yet another embodiment, the present disclosure relates to crystalline forms of reduced nicotinic acid riboside triacetate (NARH-TA, VIII), or salts, solvates, hydrates, or prodrugs thereof, and methods of preparation thereof.

The compounds and derivatives of the present invention, or salts, hydrates, solvates, or prodrugs thereof, or crystal forms thereof, aim at modulating the absorption of vitamins or bioactive compounds of known therapeutic and nutraceutical value by conjugating said vitamins or bioactive compounds to specific B3 vitamins.

The compounds and derivatives of the present invention, or salts, hydrates, solvates, or prodrugs thereof, or crystal forms thereof, provide improvements on the individual nutrients and B-vitamins in terms of modulating their bioavailabilities.

The compounds and derivatives of the present invention, or salts, hydrates, or solvates thereof, or crystal forms thereof, can be used to reduce the risk of developing symptoms, diseases, disorders, or conditions associated with, or having etiologies involving, vitamin B3 deficiencies and/or that would benefit from increased mitochondrial activity, as the key component is nicotinic acid riboside (NAR).

A rationale for synergy between vitamins B1, B2, B3, and B6 is explained herein. Pairing vitamins B1, B2, or B6 with nicotinamide riboside (NR) is hypothesized to act synergistically on the $NAD^+$ biosynthetic pathway and have a positive effect. This is due to the fact that vitamins B1, B2, and B6 are required for $NAD^+$ biosynthesis through NAMPT-dependent pathways, allowing for the further recycling of nicotinamide (Nam or NM) generated from the NR-produced $NAD^+$. Of all the B3-vitamins, only NR functions independently of NAMPT for $NAD^+$ synthesis, in a mole to mole perspective. See Penberthy & Kirkland, 2012. See also Yuling Chi & Anthony A. Sauve, *Nicotinamide riboside, a trace nutrient in foods, is a vitamin B3 with effects on energy metabolism and neuroprotection*, 16 CURR. OPINION IN CLIN. NUTRITION & METABOLIC CARE 657 (2013), incorporated by reference herein in its entirety. Additionally, vitamin B2 (FAD precursor) is a key vitamin for mitochondrial fatty acid oxidation and OXPHOS processes. Mitochondrial dysfunction can arise from FAD/FADH2 imbalance or deficiency, and it is hypothesized that pairing vitamin B2 to vitamin B3 NAD-precursors would address multiple pathways of mitochondrial dysfunction.

One embodiment of the compounds and derivatives of the present invention, or salts, hydrates, solvates, or prodrugs thereof, or crystal forms thereof, is represented by the products formed as a result of joining the nicotinic acid (NA) ester at the 5'-hydroxy of NR and NAR, and the corresponding reduced forms thereof. Synergistic effects of nicotinate and NR (or derivatives thereof) are anticipated. Nicotinic acid (NA) and nicotinamide riboside (NR) use different pathways to both ultimately induce $NAD^+$ levels.

Another embodiment of the compounds and derivatives of the present invention, or salts, hydrates, solvates, or prodrugs thereof, or crystal forms thereof, is represented by the derivatives of all of these nicotinoyl riboside conjugates and reduced nicotinoyl riboside conjugates, or salts, hydrates, solvates, or prodrugs thereof.

Nicotinoyl ribosides such as nicotinamide riboside (NR) and nicotinic acid riboside ("NAR"), nicotinamide mononucleotide (NMN), and $NAD^+$ are viewed as useful bioavailable precursors of the NAD(P)(H) pool to combat and treat a broad range of non-communicable diseases, in particular those associated with mitochondrial dysfunction and impaired cellular metabolism. Optimizing the large-scale syntheses of these vitamin B3 derivatives is therefore highly valuable to make these compounds more widely available to society both in terms of nutraceutical and pharmaceutical entities.

Crystalline forms of useful molecules can have advantageous properties relative to the respective amorphous forms of such molecules. For example, crystal forms are often easier to handle and process, for example, when preparing compositions that include the crystal forms. Crystalline forms typically have greater storage stability and are more amenable to purification. The use of a crystalline form of a pharmaceutically useful compound can also improve the performance characteristics of a pharmaceutical product that includes the compound. Obtaining the crystalline form also serves to enlarge the repertoire of materials that formulation scientists have available for formulation optimization, for example by providing a product with different properties, e.g., better processing or handling characteristics, improved dissolution profile, or improved shelf-life.

Definitions

Nicotinic acid riboside (NAR) is a pyridinium compound having the formula (I):

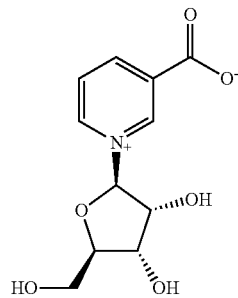

(I)

The free hydrogens of the hydroxyl groups on the ribose moiety of nicotinic acid riboside (NAR, I) can be substituted with acetyl groups (CH$_3$—C(=O)—) to form an NAR derivative, specifically 1-(2',3',5'-triacetyl-beta-D-ribofuranosyl)-nicotinic acid ("NAR triacetate" or "NARTA"), having the formula (II). Alternative names include: 1-(2',3',5')-triacetyl-beta-D-ribofuranosyl)-nicotinic acid, or 1-(3-carboxyl-pyridin-1-yl)-beta-D-riboside-2',3',5'-triacetate ("NAR triacetate" or "NARTA"), all having the formula (II):

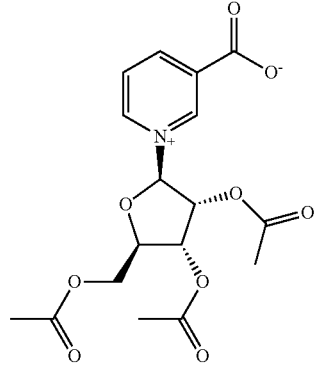

(II)

Nicotinamide riboside ("NR") is a pyridinium compound having the formula (III):

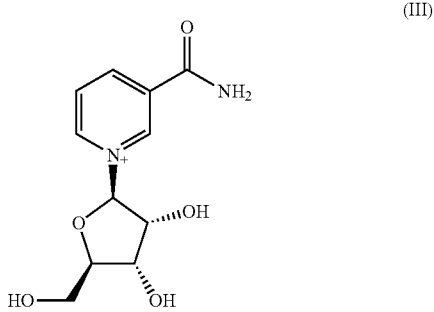 [SMILES: NC(=O)c1ccc[n+]([C@@H]2O[C@H](CO)[C@@H](O)[C@H]2O)c1]

(III)

Reduced nicotinamide riboside ("NRH") is a 1,4-dihydropyridyl reduced nicotinyl compound having the formula (IV):

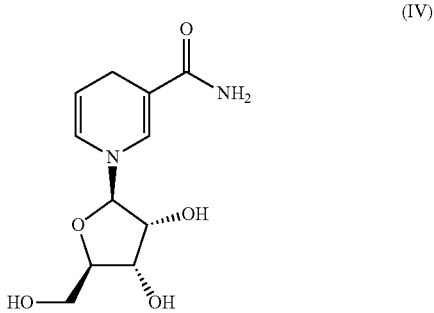 [SMILES: NC(=O)C1=CN([C@@H]2O[C@H](CO)[C@@H](O)[C@H]2O)C=CC1]

(IV)

Reduced nicotinic acid riboside ("NARH") is a 1,4-dihydropyridyl reduced nicotinyl compound having the formula (V):

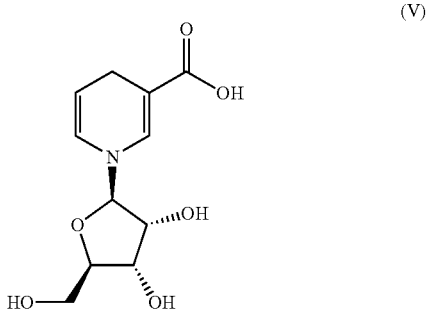

(V)

The free hydrogens of hydroxyl groups on the ribose moiety of nicotinamide riboside (NR, IV) can be substituted with acetyl groups (CH$_3$—C(=O)—) to form 1-(2',3',5'-triacetyl-beta-D-ribofuranosyl)-nicotinamide ("NR triacetate" or "NRTA") having the formula (VI):

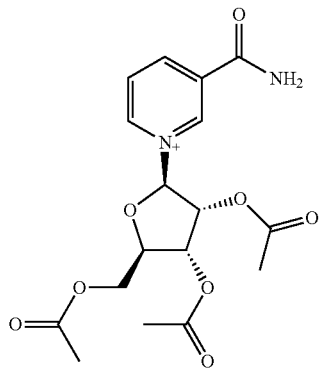

(VI)

The free hydrogens of hydroxyl groups on the ribose moiety of reduced nicotinamide riboside (NRH, IV) can be substituted with acetyl groups (CH$_3$—C(=O)—) to form 1-(2',3',5'-triacetyl-beta-D-ribofuranosyl)-1,4-dihydronicotinamide ("NRH triacetate" or "NRH-TA") having the formula (VII):

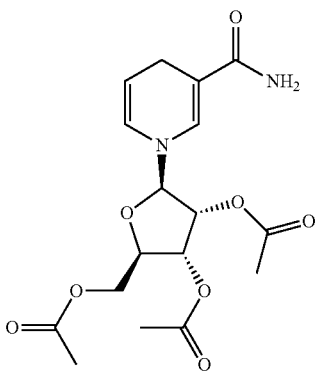

(VII)

The free hydrogens of hydroxyl groups on the ribose moiety of reduced nicotinic acid riboside (NARH, V) can be substituted with acetyl groups (CH$_3$—C(=O)—) to form 1-(2',3',5'-triacetyl-beta-D-ribofurnoasyl)-1,4-dihydronicotinic acid ("NARH triacetate" or "NARH-TA") having the formula (VIII):

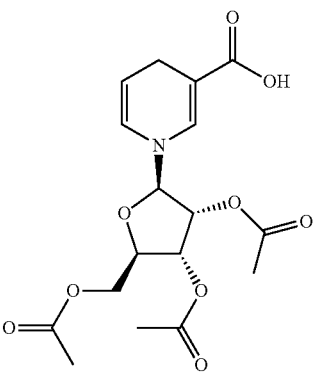

(VIII)

As used in the specification and the appended claims, the singular forms of "a," "an," and "the" include plural referents unless the context clearly dictates otherwise.

As used herein, the term "solvent" refers to a compound or mixture of compounds including, but not limited to, water, water in which an ionic compound has been dissolved, acetic acid, acetone, acetonitrile, benzene, 1-butanol, 2-butanol, t-butyl alcohol ("TBA"), 2-butanone, carbon tetrachloride, chlorobenzene, chloroform, cyclohexane, 1,2-dichloroethane ("DCE"), diethylene glycol, diethyl ether ("Et$_2$O"), diglyme (diethylene glycol dimethyl ether), 1,2-dimethoxyethane ("DME"), N,N-dimethylformamide ("DMF"), dimethylsulfoxide ("DMSO"), 1,4-dioxane, ethanol, ethyl acetate ("EtOAc"), ethylene glycol, glycerin, heptanes, hexamethylphosphoramide ("HMPA"), hexamethylphosphorus triamide ("HMPT"), hexane, methanol ("MeOH"), methyl t-butyl ether ("MTBE"), methylene chloride ("DCM," "CH$_2$Cl$_2$"), N-methyl-2-pyrrolidinone ("NMP"), nitromethane, pentane, petroleum ether, 1-propanol ("n-propanol," "n-PrOH"), 2-propanol ("isopropanol," "iPrOH"), pyridine, tetrahydrofuran ("THF"), toluene, triethylamine ("TEA," "Et$_3$N"), o-xylene, m-xylene, and/or p-xylene, and the like. Solvent classes may include hydrocarbon, aromatic, aprotic, polar, alcoholic and mixtures thereof.

According to particular embodiments, the compounds or derivatives prepared according to embodiments of the methods of the present disclosure can comprise compounds or derivatives, or salts, hydrates, solvates, or prodrugs thereof, or crystalline forms thereof, substantially free of solvents or other by-products, generally, or a particular solvent or by-product. In certain embodiments, by "substantially free" is meant greater than about 80% free of solvents or by-products, or greater than about 80% free of a particular solvent or by-product, more preferably greater than about 90% free of solvents or by-products, or greater than about 90% free of a particular solvent or by-product, even more preferably greater than about 95% free of solvents or by-products, or greater than about 95% free of a particular solvent or by-product, even more preferably greater than about 98% free of solvents or by-products, or greater than about 98% free of a particular solvent or by-product, even more preferably greater than about 99% free of solvents or by-products, or greater than about 99% free of a particular solvent or by-product, even more preferably greater than about 99.99% free of solvents or by-products, or greater than about 99.99% free of a particular solvent or by-product, and most preferably quantitatively free of solvents or by-products, or quantitatively free of a particular solvent or by-product.

According to particular embodiments, the compounds or derivatives prepared according to embodiments of the methods of the present disclosure can comprise compounds or derivatives, or salts, hydrates, solvates, or prodrugs thereof, or crystalline forms thereof, substantially free of solvents or other by-products, generally, or a particular solvent or by-product. In certain embodiments, by "substantially free" is meant less than about 10,000 ppm of solvents or by-products, or less than about 10,000 ppm of a particular solvent or by-product, even more preferably less than about 1,000 ppm of solvents or by-products, or less than about 1,000 ppm of a particular solvent or by-product, even more preferably less than about 100 ppm of solvents or by-products, or less than about 100 ppm of a particular solvent or by-product, even more preferably less than about 10 ppm of solvents or by-products, or less than about 10 ppm of a particular solvent or by-product, even more preferably less than 5 ppm of solvents or by-products, or less than 5 ppm of a particular solvent or by-product, and most preferably, an undetectable amount of solvents or by-products, or an undetectable amount of a particular solvent or by-product.

Preparation of Crystalline Forms of Nicotinic Acid Riboside (NAR, I) and Nicotinic Acid Riboside Triacetate (NARTA, II), or Salts, Hydrates, Solvates, or Prodrugs Thereof In an embodiment, a method of making a crystalline Form II of nicotinic acid riboside (NAR, I) can include the steps of:

(a) adding a volume of hexafluoroisopropanol to a mass of nicotinic acid riboside (NAR, I) in a vessel, optionally, such that the mass (mg) to volume (mL) ratio of nicotinic acid riboside (NAR, I) to hexafluoroisopropanol is about 36:1;

(b) dissolving the mass of nicotinic acid riboside (NAR, I) in the volume of hexafluoroisopropanol so as to produce a solution of nicotinic acid riboside (NAR, I) in hexafluoroisopropanol;

optionally, (b1) filtering the solution of nicotinic acid riboside (NAR, I) in hexafluoroisopropanol;

(c) adding the solution of nicotinic acid riboside (NAR, I) in hexafluoroisopropanol to an open vessel;

(d) placing the open vessel containing the solution of nicotinic acid riboside (NAR, I) in hexafluoroisopropanol inside a larger vessel containing a volume of ethyl acetate that is approximately equal to the volume of the solution of nicotinic acid riboside (NAR, I) in hexafluoroisopropanol;

(e) sealing the larger vessel;

(f) maintaining the solution of nicotinic acid riboside (NAR, I) in hexafluoroisopropanol at ambient temperature so as to crystallize the crystalline Form II of nicotinic acid riboside (NAR, I);

optionally, (f1) unsealing the larger vessel;

optionally, (f2) adding an additional volume of ethyl acetate to the larger vessel that is approximately half of the volume of ethyl acetate contained in the larger vessel according to step (d);

optionally, (f3) maintaining the solution of nicotinic acid riboside (NAR, I) in hexafluoroisopropanol at ambient temperature;

(g) unsealing the larger vessel;

(h) removing the open vessel from the larger vessel; and (i) isolating the crystalline Form II of nicotinic acid riboside (NAR, I).

The process described herein effects a preparation of a crystalline Form II of nicotinic acid riboside (NAR, I). Acceptable mass (mg) to volume (mL) ratios of nicotinic acid riboside (NAR, I) to hexafluoroisopropanol can be from about 1:1 to about 50:1.

In another embodiment, a method of making a crystalline Form II of nicotinic acid riboside (NAR, I) can include the steps of:

(a) adding a volume of hexafluoroisopropanol to a mass of nicotinic acid riboside (NAR, I) in a vessel, optionally, such that the mass (mg) to volume (mL) ratio of nicotinic acid riboside (NAR, I) to hexafluoroisopropanol is about 36:1;

(b) dissolving the mass of nicotinic acid riboside (NAR, I) in the volume of hexafluoroisopropanol so as to produce a solution of nicotinic acid riboside (NAR, I) in hexafluoroisopropanol;

optionally, (b1) filtering the solution of nicotinic acid riboside (NAR, I) in hexafluoroisopropanol;

(c) adding the solution of nicotinic acid riboside (NAR, I) in hexafluoroisopropanol to an open vessel;

(d) placing the open vessel containing the solution of nicotinic acid riboside (NAR, I) in hexafluoroisopropanol inside a larger vessel containing a volume of ethyl acetate that is approximately equal to the volume of the solution of nicotinic acid riboside (NAR, I) in hexafluoroisopropanol;

(e) sealing the larger vessel;

(f) maintaining the solution of nicotinic acid riboside (NAR, I) in hexafluoroisopropanol at ambient temperature for at least 7 days so as to crystallize the crystalline Form II of nicotinic acid riboside (NAR, I);

optionally, (f1) unsealing the larger vessel;

optionally, (f2) adding an additional volume of ethyl acetate to the larger vessel that is approximately half of the volume of ethyl acetate contained in the larger vessel according to step (d);

optionally, (f3) maintaining the solution of nicotinic acid riboside (NAR, I) in hexafluoroisopropanol at ambient temperature for at least 7 days;

(g) unsealing the larger vessel;

(h) removing the open vessel from the larger vessel; and (i) isolating the crystalline Form II of nicotinic acid riboside (NAR, I).

The process described herein effects a preparation of a crystalline Form II of nicotinic acid riboside (NAR, I). Acceptable mass (mg) to volume (mL) ratios of nicotinic acid riboside (NAR, I) to hexafluoroisopropanol can be from about 1:1 to about 50:1.

In an embodiment, a method of making a crystalline Form II of nicotinic acid riboside triacetate (NARTA, II) can include the steps of:

(a) adding a volume of ethanol to a mass of nicotinic acid riboside triacetate (NARTA, II) in a vessel, optionally, such that the mass (mg) to volume (mL) ratio of nicotinic acid riboside triacetate (NARTA, II) to ethanol is about 67:1;

(b) dissolving the mass of nicotinic acid riboside triacetate (NARTA, II) in the volume of ethanol at approximately 50° C. so as to produce a solution of nicotinic acid riboside triacetate (NARTA, II) in ethanol;

(c) cooling the solution of nicotinic acid riboside triacetate (NARTA, II) in ethanol at −20° C. so as to crystallize the crystalline Form II of nicotinic acid riboside triacetate (NARTA, II); and (d) isolating the crystalline Form II of nicotinic acid riboside triacetate (NARTA, II).

The process described herein effects a preparation of a crystalline Form II of nicotinic acid riboside triacetate (NARTA, II). Acceptable mass (mg) to volume (mL) ratios of nicotinic acid riboside triacetate (NARTA, II) to ethanol can be from about 50:1 to about 100:1.

In another embodiment, a method of making a crystalline Form II of nicotinic acid riboside triacetate (NARTA, II) can include the steps of:

(a) adding a volume of ethanol to a mass of nicotinic acid riboside triacetate (NARTA, II) in a vessel, optionally, such that the mass (mg) to volume (mL) ratio of nicotinic acid riboside triacetate (NARTA, II) to ethanol is about 67:1;

(b) dissolving the mass of nicotinic acid riboside triacetate (NARTA, II) in the volume of ethanol at approximately 50° C. so as to produce a solution of nicotinic acid riboside triacetate (NARTA, II) in ethanol;

(c) cooling the solution of nicotinic acid riboside triacetate (NARTA, II) in ethanol at −20° C. for at least 24 hours so as to crystallize the crystalline Form II of nicotinic acid riboside triacetate (NARTA, II); and (d) isolating the crystalline Form II of nicotinic acid riboside triacetate (NARTA, II).

The process described herein effects a preparation of a crystalline Form II of nicotinic acid riboside triacetate (NARTA, II). Acceptable mass (mg) to volume (mL) ratios of nicotinic acid riboside triacetate (NARTA, II) to ethanol can be from about 50:1 to about 100:1.

The crystalline forms of nicotinic acid riboside (NAR, I) and nicotinic acid riboside triacetate (NARTA, II) of the present disclosure may be isolated from their reaction mixtures and purified by standard techniques such as filtration, liquid-liquid extraction, solid phase extraction, distillation, recrystallization, or chromatography, including flash column chromatography, preparative TLC, HPTLC, HPLC, or rp-HPLC. One preferred method for preparation of the crystalline forms of nicotinic acid riboside (NAR, I) and nicotinic acid riboside (NARTA, II) of the present disclosure, comprises crystallizing the compound, or salt, hydrate, solvate, or prodrug thereof, from a solvent, to form, preferably, a crystalline form of the compound or derivative, or salt, hydrate, solvate, or prodrug thereof. Following crystallization, the crystallization solvent is removed by a process other than evaporation, for example, filtration or decanting, and the crystals are then preferably washed using pure solvent (or a mixture of pure solvents). Preferred solvents for crystallization include water; alcohols, particularly alcohols containing up to four carbon atoms, such as methanol, ethanol, isopropanol, butan-1-ol, butan-2-ol, and 2-methyl-2-propanol; ethers, for example diethyl ether, diisopropyl ether, t-butyl methyl ether, 1,2-dimethoxyethane, tetrahydrofuran, and 1,4-dioxane; carboxylic acids, for example formic acid and acetic acid; hydrocarbon solvents, for example pentane, hexane, and toluene; and mixtures thereof, particularly aqueous mixtures such as aqueous methanol, ethanol, isopropanol, and acetone. Pure solvents, preferably at least analytical grade, and more preferably pharmaceutical grade are preferably used. In preferred embodiments of the methods of the invention, the crystalline forms are so isolated.

Crystalline Forms Isolated as Salts of Nicotinic Acid Riboside (NAR, I) and Nicotinic Acid Riboside Triacetate (NARTA, II) According to the Methods of the Present Disclosure The crystalline forms of nicotinic acid riboside (NAR, I) and nicotinic acid riboside triacetate (NARTA, II) that are prepared by the methods of the present disclosure may take the form of salts. The term "salts" embraces addition salts of free acids or free bases that are crystalline forms of nicotinic acid riboside (NAR, I) and nicotinic acid riboside triacetate (NARTA, II) that are prepared by the methods of the present disclosure. The term "pharmaceutically acceptable salt" refers to salts that possess toxicity profiles within a range that affords utility in pharmaceutical applications.

Suitable pharmaceutically acceptable acid addition salts may be prepared from an inorganic acid or from an organic acid. Examples of inorganic acids include hydrochloric, hydrobromic, hydroiodic, nitric, carbonic, sulfuric, and phosphoric acids. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoroacetic, triflorometh-anesulfonic, 2-hydroxyethanesulfonic, p-toluenesulfonic, sulfanilic, cyclohexylaminosulfonic, stearic, alginic, β-hydroxybutyric, salicylic, galactaric, and galacturonic acid. In the present examples of crystalline forms of nicotinic acid riboside (NAR, I) and nicotinic acid riboside triacetate (NARTA, II), or salts, hydrates, solvates, or prodrugs thereof, i.e., compounds containing amino groups, pyridine, or reduced pyridine, said compounds can be isolated as salts of inorganic acids or strong organic acids, e.g., hydrochloric acid or trifluoroacetic acid.

Suitable pharmaceutically acceptable base addition salts include, for example, metallic salts including alkali metal, alkaline earth metal, and transition metal salts such as, for example, calcium, magnesium, potassium, sodium, and zinc salts. Further, base addition salts include, for example, ammonium salts. Pharmaceutically acceptable base addition salts also include organic salts made from basic amines such as, for example, N,N-dibenzylethelenediamine, chloroprocaine, choline, diethanolamine, ethylenediamine, meglumine (N-methylglucamine), tromethamine (tris(hydroxymethyl)aminomethane), and procaine.

Preferably, suitable pharmaceutically acceptable salts of nicotinic acid riboside (NAR, I), or nicotinic acid riboside triacetate (NARTA, II), may include, but are not limited to, salts containing an anion selected from the group consisting of fluoride, chloride, bromide, iodide, formate, acetate, propionate, butyrate, glutamate, asparatate, ascorbate, benzoate, carbonate, citrate, carbamate, gluconate, lactate, succinate, nitrate, and sulfate.

All of these salts may be prepared by conventional means from nicotinic acid riboside (NAR, I) or nicotinic acid riboside triacetate (NARTA, II), or salts, hydrates, solvates or prodrugs thereof, by reacting, for example, the appropriate acid or base with nicotinic acid riboside (NAR, I), or nicotinic acid riboside triacetate (NARTA, II), or salts, hydrates, solvates, or prodrugs thereof. Preferably, the salts are in crystalline form, or alternative in dried or freeze-dried form. The person skilled in the art will know how to prepare and select suitable salt forms for example, as described in P. H. STAHL & C. G. WERMUTH, HANDBOOK OF PHARMACEUTICAL SALTS: PROPERTIES, SELECTION, AND USE (Wiley-VCH 2002).

The nutraceutical compositions of the present disclosure may be administered in combination with a nutraceutically acceptable carrier. The active ingredients in such formulations may comprise from 1% by weight to 99% by weight, or alternatively, 0.1% by weight to 99.9% by weight. "Nutraceutically acceptable carrier" means any carrier, diluents, or excipient that is compatible with the other ingredients of the formulation and not deleterious to the user. In accordance with one embodiment, suitable nutraceutically acceptable carriers can include ethanol, aqueous ethanol mixtures, water, fruit, and/or vegetable juices, and combinations thereof.

Delivery System

Suitable dosage forms include tablets, capsules, solutions, suspensions, powders, gums, and confectionaries. Sublingual delivery systems include, but are not limited to, dissolvable tabs under and on the tongue, liquid drops, and beverages. Edible films, hydrophilic polymers, oral dissolvable films, or oral dissolvable strips can be used. Other useful delivery systems comprise oral or nasal sprays or inhalers, and the like.

For oral administration, crystalline forms of nicotinic acid riboside (NAR, I) or nicotinic acid riboside triacetate (NARTA, II), or a salt, hydrate, solvate, or prodrug thereof may be further combined with one or more solid inactive ingredients for the preparation of tablets, capsules, pills, powders, granules, or other suitable dosage forms. For example, the active agent may be combined with at least one excipient such as fillers, binders, humectants, disintegrating agents, solution retarders, absorption accelerators, wetting agents, absorbents, or lubricating agents. Other useful excipients include magnesium stearate, calcium stearate, mannitol, xylitol, sweeteners, starch, carboxymethylcellulose, microcrystalline cellulose, silica, gelatin, silicon dioxide, and the like.

The crystalline forms of nicotinic acid riboside (NAR, I) or nicotinic acid riboside triacetate (NARTA, II), or a salt, hydrate, solvate, or prodrug thereof, prepared according to the methods of the present disclosure, together with a conventional adjuvant, carrier, or diluent, may thus be placed into the form of pharmaceutical compositions and unit dosages thereof. Such forms include solids, and in particular, tablets, filled capsules, powder, and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principals, and such unit dosage forms may contain any suitable effective amount of the active ingredient commensurate with the intended daily dosage range to be employed.

The crystalline forms of nicotinic acid riboside (NAR, I) or nicotinic acid riboside triacetate (NARTA, II) prepared according to the methods of the present disclosure can be administered in a wide variety of oral and parenteral dosage forms. It will be obvious to those skilled in the art that the following dosage forms may comprise, as the active component, a crystalline form of nicotinic acid riboside (NAR, I) or nicotinic acid riboside triacetate (NARTA, II) prepared according to the methods of the present disclosure or a crystalline form of a pharmaceutically acceptable salt, hydrate, solvate, or prodrug of nicotinic acid riboside (NAR, I) or nicotinic acid riboside triacetate (NARTA, II) prepared according to the methods of the present disclosure.

For preparing pharmaceutical compositions from a crystalline form of nicotinic acid riboside (NAR, I) or nicotinic acid riboside triacetate (NARTA, II), or a salt, hydrate, solvate, or prodrug thereof, prepared according to the methods of the present disclosure, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, solubilizers, lubricants, suspending agents, binders, preservatives, tablet disintegrating agents, or an encapsulating material.

In powders, the carrier is a finely divided solid, which is in a mixture with the finely divided active components. In tablets, the active component is mixed with the carrier having the necessary binding capacity in suitable proportions and compacted in the shape and size desired.

The powders and tablets preferably contain from about five or ten to about seventy percent of the active crystalline form of nicotinic acid riboside (NAR, I) or nicotinic acid riboside triacetate (NARTA, II), or salt, hydrate, solvate, or prodrug thereof, prepared according to the methods of the present disclosure. Suitable carriers are microcrystalline cellulose, sugar, lactose, pectin, dextrin, starch, gelatin, tragacanth, methylcellulose, sodium carboxymethylcellulose, a low melting wax, cocoa butter, and the like, and other excipients may include magnesium stearate, stearic acid, talc, silicon dioxide, etc. The term "preparation" is intended to include the formulation of active compound with encapsulating material as carrier providing a capsule in which the active component, with or without carriers, is surrounded by a carrier, which is thus in association with it. Tablets, powders, capsules, pills, sachets, and lozenges are included. Tablets, powders, capsules, pills, sachets, and lozenges can be used as solid forms suitable for oral administration.

Liquid preparations include solutions, suspensions, and emulsions, for example, water or water-propylene glycol solutions. For example, parenteral injection liquid preparations can be formulated as solutions in aqueous polyethylene glycol solution. The crystalline forms of nicotinic acid riboside (NAR, I) or nicotinic acid riboside triacetate (NARTA, II), or salts, hydrates, solvates, or produgs thereof prepared according to the methods of the present disclosure may thus be formulated for parenteral administration (e.g., by injection, for example bolus injection or continuous infusion) and may be presented in unit dose for example in ampoules, pre-filled syringes, small volume infusion, or in multi-dose containers with an added preservative). The compositions may take such forms as suspensions, solutions, or emulsions in oily or aqueous vehicles, and may contain formulation agents such as suspending, stabilizing, and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

Aqueous solutions suitable for oral use can be prepared by dissolving the active component in water and adding suitable colorants, flavors, stabilizing and thickening agents, as desired. Aqueous suspensions suitable for oral use can be made by dispersing the finely divided active component in water with viscous material, such as natural or synthetic gums, resins, methylcellulose, sodium carboxymethylcellulose, or other well-known suspending agents.

Compositions suitable for topical administration in the mouth include lozenges comprising the active agent in a flavored base, usually sucrose and acacia or tragacanth; pastilles comprising the active ingredient in an inert base such as gelatin and glycerine or sucrose and acacia; and mouthwashes comprising the active ingredient in suitable liquid carrier.

Solutions or suspensions are applied directly to the nasal cavity by conventional means, for example, with a dropper, pipette, or spray. The compositions may be provided in single or multi-dose form. In compositions intended for administration to the respiratory tract, including intranasal compositions, the crystalline form will generally have a small particle size, for example, of the order of 5 microns or less. Such a particle size may be obtained by means known in the art, for example by micronization.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets, capsules, and lozenges for oral administration and liquids for oral use are preferred compositions. Solutions or suspensions for application to the nasal cavity or to the respiratory tract are preferred compositions. Transdermal patches for topical administration to the epidermis are preferred.

Further details on techniques for formulation and administration may be found in the latest edition of Remington's Pharmaceutical Sciences (Mack Publishing Co., Easton, Pa.).

Solid nutritional compositions for oral administration may optionally contain, in addition to the above enumerated nutritional composition ingredients or compounds: carrier materials such as corn starch, gelatin, acacia, microcrystalline cellulose, kaolin, dicalcium phosphate, calcium carbonate, sodium chloride, alginic acid, and the like; binders including acacia, methylcellulose, sodium carboxymethylcellulose, polyvinylpyrrolidone, hydroxypropyl methylcellulose, ethyl cellulose, and the like; and lubricants such as magnesium stearate, stearic acid, silicone fluid, talc, waxes, oils, colloidal silica, and the like. The usefulness of such excipients is well known in the art.

Liquid nutritional compositions for oral administration in connection with a method for preventing and/or treating inflammation, colds, and/or flu can be prepared in water or other aqueous vehicles. In addition to the above enumerated ingredients or compounds, liquid nutritional compositions can include suspending agents such as, for example, methylcellulose, alginates, tragacanth, pectin, legin, carrageenan, acacia, polyvinylpyrrolidone, polyvinyl alcohol, and the like. The liquid nutritional compositions can be in the form of a solution, emulsion, syrup, gel, or elixir including or containing, together with the above enumerated ingredients or compounds, wetting agents, sweeteners, and coloring and flavoring agents. Various liquid and powder nutritional compositions can be prepared by conventional methods. Various ready-to-drink formulations ("RTDs") are contemplated.

Routes of Administration

The compositions may be administered by any suitable route, including but not limited to oral, sublingual, buccal, ocular, pulmonary, rectal, and parenteral administration, or as an oral or nasal spray (e.g., inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. Also contemplated within the scope of the invention is the installation of a pharmaceutical composition in the body of the patient in a controlled formulation, with systemic or local release of the drug to occur at a later time. For example, the drug may be localized in a depot for controlled release to the circulation, or for release to a local site.

Pharmaceutical compositions of the disclosure may be those suitable for oral, rectal, bronchial, nasal, pulmonal, topical (including buccal and sub-lingual), transdermal, vaginal, or parenteral (including cutaneous, subcutaneous, intramuscular, intraperitoneal, intravenous, intraarterial, intracerebral, intraocular injection, or infusion) administration, or those in a form suitable for administration by inhalation or insufflations, including powders and liquid aerosol administration, or by sustained release systems. Suitable examples of sustained release systems include semipermeable matrices of solid hydrophobic polymers containing a crystalline form of nicotinic acid riboside (NAR, I) or nicotinic acid riboside triacetate (NARTA, II), or a salt, hydrate, solvate, or prodrug thereof, prepared according to the methods of the present disclosure, which matrices may be in the form of shaped articles, e.g., films or microcapsules.

The methods described above may be further understood in connection with the following Examples. In addition, the following non-limiting examples are provided to illustrate the invention. The illustrated preparation procedures are applicable to other embodiments of the present invention. The preparation procedures described as general methods describe what is believed will be typically effective to perform the preparation indicated. However, the person skilled in the art will appreciate that it may be necessary to vary the procedures for any given embodiment of the invention, e.g., vary the order or steps and/or the chemical reagents used. Products may be purified by conventional techniques that will vary, for example, according to the physical properties of the crystalline forms prepared according to the methods of the present invention.

Example 1

Preparation of Crystalline Form II of Nicotinic Acid Riboside (NAR, I) by Vapor Diffusion in Hexafluoroisopropanol ("HFIPA") with Ethyl Acetate ("EtOAc") as an Anti-solvent.

1.5 milliliters of a solution of nicotinic acid riboside (NAR, I, 182.5 milligrams) in hexafluoroisopropanol (HFIPA, 5 milliliters) was filtered through a 0.2-µm PTFE syringe filter into a clean, 1-dram vial. The uncapped vial was placed into a 20-milliliter vial containing 2.0 milliliters of ethyl acetate (EtOAc). The 20-milliliter vial was capped and left at ambient conditions for 7 days. An additional 1.0 milliliter of EtOAc was added to the 20-milliliter vial. The 20-milliliter vial was capped and left at ambient conditions for an additional 6 days. White solids on the bottom and sides of the 1-dram vial in a clear solution were observed. The solution was decanted with a disposable pipette and the remaining solids were dried, briefly, under nitrogen ("$N_2$") atmosphere.

The crystalline Form II of nicotinic acid riboside (NAR, I) may be characterized by a powder X-ray diffraction pattern having peaks at 16.9, 17.7, and 26.6 degrees two theta±0.2 degrees two theta. The crystalline Form II of nicotinic acid riboside (NAR, I) may also or alternatively be characterized by a powder X-ray diffraction pattern having peaks at 8.5, 15.8, 16.9, 17.7, and 26.6 degrees two theta±0.2 degrees two theta. The crystalline Form II of nicotinic acid riboside (NAR, I) may also or alternatively be characterized by a powder X-ray diffraction pattern having peaks at 8.5, 13.9, 15.8, 16.9, 17.7, 21.7, 22.0, 26.1, 26.6, and 27.9 degrees two theta±0.2 degrees two theta.

In other embodiments, the crystalline Form II of nicotinic acid riboside (NAR, I) may be characterized by a powder X-ray diffraction pattern substantially as shown in FIG. 1. The crystalline Form II of nicotinic acid riboside (NAR, I) may also or alternatively be characterized by a powder X-ray diffraction pattern having peaks substantially as provided in Table 1, below, ±0.2 degrees two theta.

TABLE 1

| Peak No. | Pos. [°2Th.] | d-spacing [Å] | Height [cts] | I/I$_{max}$ [%] |
|---|---|---|---|---|
| 1 | 8.5 | 10.34 | 13555 | 49 |
| 2 | 11.7 | 7.53 | 1519 | 5 |
| 3 | 13.9 | 6.36 | 7112 | 25 |
| 4 | 15.8 | 5.62 | 15566 | 56 |
| 5 | 16.9 | 5.24 | 23886 | 86 |
| 6 | 17.2 | 5.16 | 5212 | 19 |
| 7 | 17.7 | 5.00 | 27891 | 100 |
| 8 | 18.5 | 4.80 | 2627 | 9 |
| 9 | 19.2 | 4.61 | 3512 | 13 |
| 10 | 20.4 | 4.36 | 2232 | 8 |
| 11 | 21.5 | 4.12 | 3001 | 11 |
| 12 | 21.7 | 4.09 | 7301 | 26 |
| 13 | 22.0 | 4.03 | 10769 | 39 |
| 14 | 22.4 | 3.96 | 2223 | 8 |
| 15 | 23.7 | 3.75 | 1214 | 4 |
| 16 | 24.4 | 3.65 | 1476 | 5 |
| 17 | 25.3 | 3.52 | 1137 | 4 |

TABLE 1-continued

| Peak No. | Pos. [°2Th.] | d-spacing [Å] | Height [cts] | I/I$_{max}$ [%] |
|---|---|---|---|---|
| 18 | 25.6 | 3.48 | 1690 | 6 |
| 19 | 25.8 | 3.45 | 2669 | 10 |
| 20 | 26.1 | 3.41 | 7182 | 26 |
| 21 | 26.6 | 3.35 | 16269 | 58 |
| 22 | 26.9 | 3.31 | 1932 | 7 |
| 23 | 27.2 | 3.28 | 1110 | 4 |
| 24 | 27.6 | 3.22 | 2191 | 8 |
| 25 | 27.9 | 3.19 | 7870 | 28 |
| 26 | 28.9 | 3.09 | 1076 | 4 |
| 27 | 29.1 | 3.06 | 1714 | 6 |
| 28 | 31.2 | 2.86 | 2124 | 8 |
| 29 | 31.8 | 2.82 | 4838 | 17 |
| 30 | 31.8 | 2.81 | 4554 | 16 |
| 31 | 33.8 | 2.65 | 4827 | 17 |
| 32 | 34.8 | 2.57 | 1536 | 6 |
| 33 | 36.0 | 2.49 | 2820 | 10 |
| 34 | 37.3 | 2.41 | 2605 | 9 |
| 35 | 39.1 | 2.30 | 1468 | 5 |

X-ray diffraction patterns were collected with a PANalytical X'Pert Pro MPD or Empyrean diffractometer using an incident beam of Cu radiation produced using an Optix long, fine-focus source. An elliptically graded multilayer mirror was used to focus Cu Kα X-rays through the specimen and onto the detector. Soller slits for the incident and diffracted beams were used to minimize broadening from axial divergence. Diffraction patterns were collected using a scanning position-sensitive detector (X'Celerator) located 240 millimeters from the specimen and Data Collector software.

Figure 2:
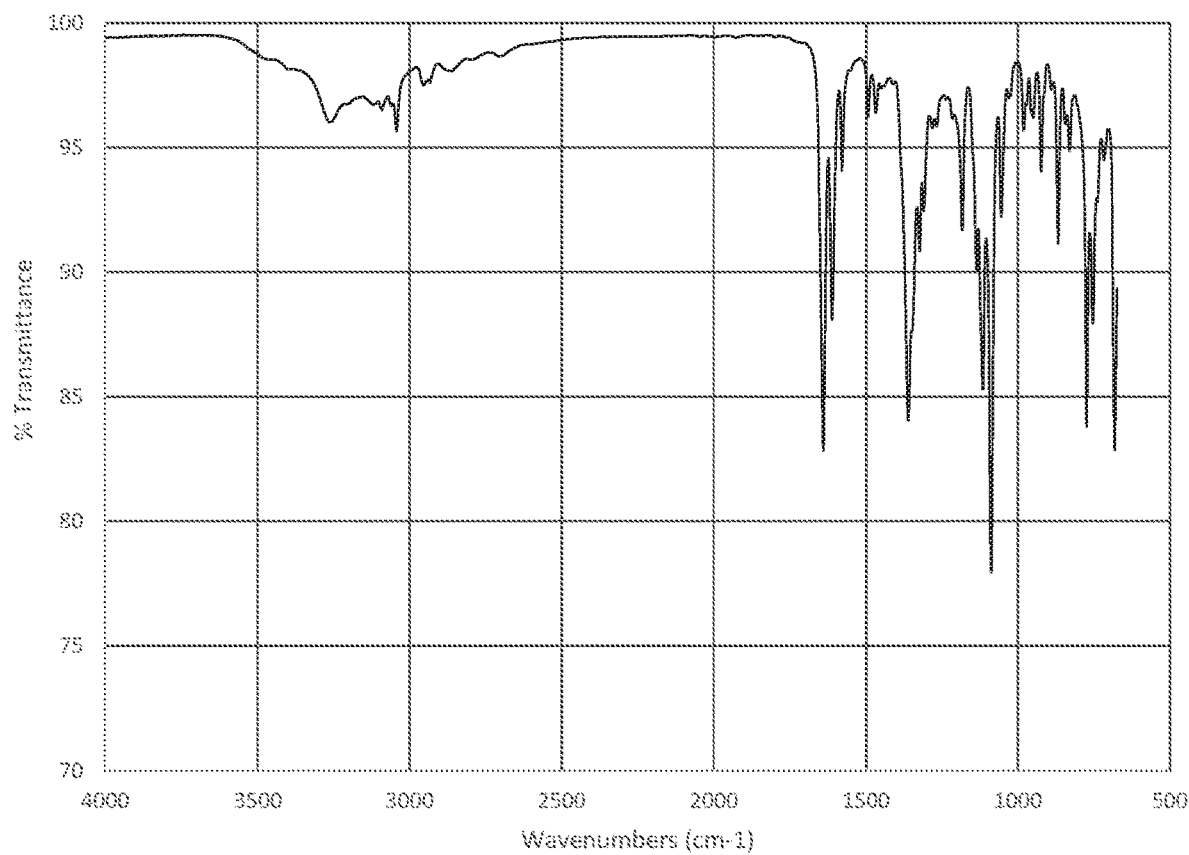
FIG. 2 provides a solid-state IR spectrum for the presently disclosed Form II of crystalline nicotinic acid riboside (NAR), the compound having formula (I), prepared according to an embodiment of the presently disclosed methods for the preparation of a crystalline form of nicotinic acid riboside (NAR).

The crystalline Form II of nicotinic acid riboside (NAR, I) may also or alternatively be characterized by a solid-state IR spectrum having peaks at 754.0, 775.3, 867.8, 923.8, and 1641.2 cm$^{-1}$±0.2 cm$^{-1}$. The crystalline Form II of nicotinic acid riboside (NAR, I) may also or alternatively be characterized by a solid-state IR spectrum having peaks at 754.0, 775.3, 867.8, 923.8, 1054.9, 1087.7, 1114.7, 1135.9, 1184.1, and 1641.2 cm$^{-1}$±0.2 cm$^{-1}$. The crystalline Form II of nicotinic acid riboside (NAR, I) may also or alternatively be characterized by a solid-state IR spectrum having peaks at 754.0, 775.3, 867.8, 923.8, 1054.9, 1087.7, 1114.7, 1135.9, 1184.1, 1309.5, 1322.9, 1359.6, and 1641.2 cm$^{-1}$±0.2 cm$^{-1}$. The crystalline Form II of nicotinic acid riboside (NAR, I) may also or alternatively be characterized by a solid-state IR spectrum having peaks at 754.0, 775.3, 867.8, 923.8, 1054.9, 1087.7, 1114.7, 1135.9, 1184.1, 1309.5, 1322.9, 1359.6, 1579.4, 1612.2, 1641.2, 3043.2, and 3259.2 cm$^{-1}$±0.2 cm$^{-1}$. In certain embodiments, the crystalline Form II of nicotinic acid riboside (NAR, I) may also or alternatively be characterized by a solid-state IR spectrum substantially as shown in FIG. 2. In further embodiments, the crystalline Form II of nicotinic acid riboside (NAR, I) may also or alternatively be characterized by a solid-state IR spectrum having transmittance peaks substantially as provided in Table 2, below, ±0.2 cm$^{-1}$.

TABLE 2

| IR (cm$^{-1}$) |
|---|
| 3259.16 |
| 3043.17 |
| 1641.22 |
| 1612.22 |
| 1579.44 |
| 1359.59 |
| 1322.94 |
| 1309.45 |
| 1184.10 |
| 1135.88 |
| 1114.67 |
| 1087.67 |
| 1054.89 |
| 923.75 |
| 867.82 |
| 775.26 |
| 754.04 |

IR spectra were acquired using a Nicolet 6700 Fourier Transform infrared ("FT-IR") spectrophotometer (Thermo Nicolet) equipped with an Ever-Glo mid/far IR source, a potassium bromide ("KBr") beamsplitter, and a deuterated triglycine sulfate ("DTGS") detector. An attenuated total reflectance ("ATR") accessory (Thunderdome™, Thermo Spectra-Tech) equipped with a germanium ("Ge") crystal was used for data acquisition. Each spectrum represents 256 co-added scans collected at a spectral resolution of 4 cm$^{-1}$.

In another embodiment, crystalline Form II of nicotinic acid riboside (NAR, I) is characterized by a DSC thermogram obtained using a heating rate of 10° C./min comprising an endothermic event with an onset temperature of 153.0° C.±2° C.

In yet another embodiment, crystalline Form II of nicotinic acid riboside (NAR, I) is characterized by a DSC thermogram obtained using a heating rate of 10° C./min comprising an endothermic event with a peak temperature of 155.9° C.±2° C.

In yet another embodiment, crystalline Form II of nicotinic acid riboside (NAR, I) is characterized by a DSC thermogram obtained using a heating rate of 10° C./min comprising an endothermic event with an onset temperature of 153° C.±2° C., a peak temperature of 155.9° C.±2° C., or both.

Figure 3:
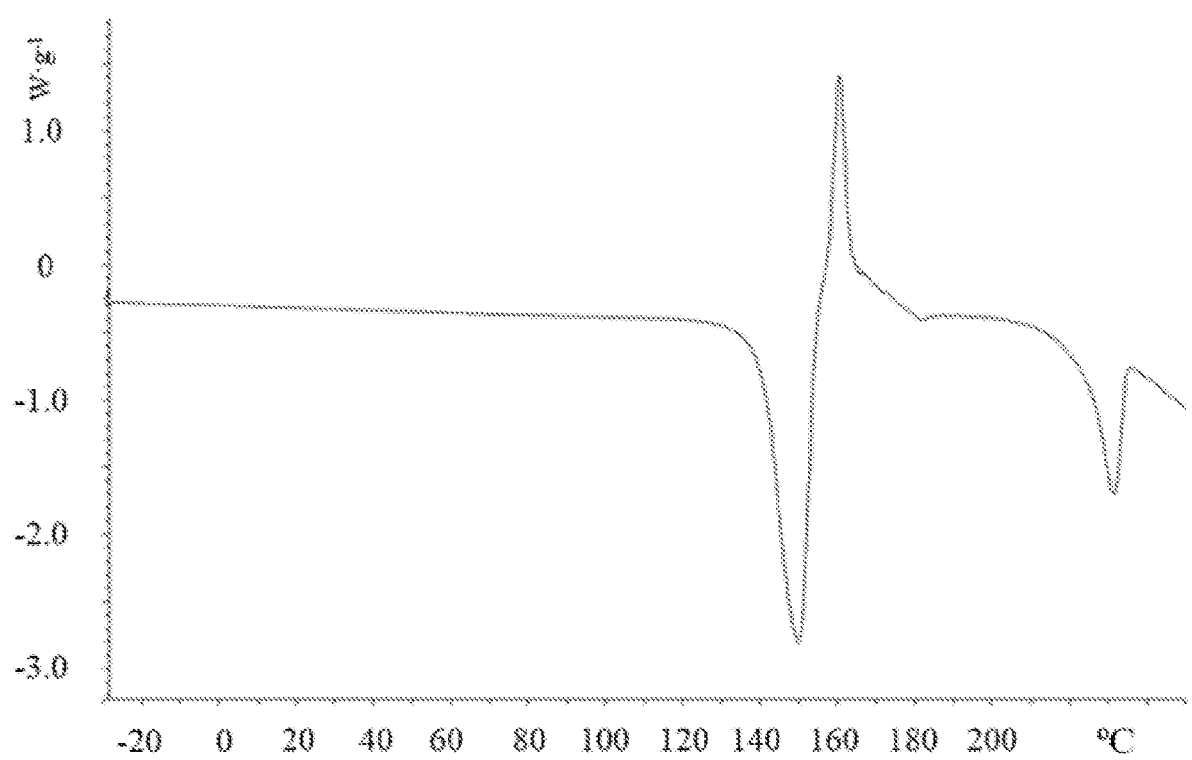
FIG. 3 provides a DSC thermogram for a sample of the presently disclosed Form II of crystalline nicotinic acid riboside (NAR) that was heated at a rate of 10° C./min.

In yet another embodiment, crystalline Form II of nicotinic acid riboside (NAR, I) may be characterized by a DSC thermogram substantially as shown in FIG. 3.

Differential Scanning Calorimetry was performed using a Mettler-Toledo DSC3+ analyzer. The samples were scanned through the temperature range (−30° C. to 250° C.) at 10° C./min (display exothermic up).

Example 2

Preparation of Crystalline Form II of Nicotinic Acid Riboside Triacetate (NARTA, II).

200 milligrams of nicotinic acid riboside triacetate (NARTA, II) was added to a scintillation vial, and 3 milliliters of ethanol was added. The mixture was added to a hot water bath at 50° C. and continuously stirred until the nicotinic acid riboside triacetate dissolved in the ethanol. The solution was placed in a freezer at −20° C. for 24 hours. The solids were vacuum filtered and then placed in a vacuum oven for 24 hours at 40° C.

The crystalline Form II of nicotinic acid riboside triacetate (NARTA, II) may be characterized by a powder X-ray diffraction pattern having peaks at 8.0, 9.7, and 19.4 degrees two theta±0.2 degrees two theta. The crystalline Form II of nicotinic acid riboside triacetate (NARTA, II) may be characterized by a powder X-ray diffraction pattern having peaks at 8.0, 9.7, 11.7, 19.0, 19.4, and 23.5 degrees two theta±0.2 degrees two theta. The crystalline Form II of nicotinic acid riboside triacetate (NARTA, II) may be characterized by a powder X-ray diffraction pattern having peaks at 8.0, 9.7, 11.7, 12.6, 14.7, 16.8, 19.0, 19.4, 22.4, 23.5, and 25.1 degrees two theta±0.2 degrees two theta.

Figure 4:
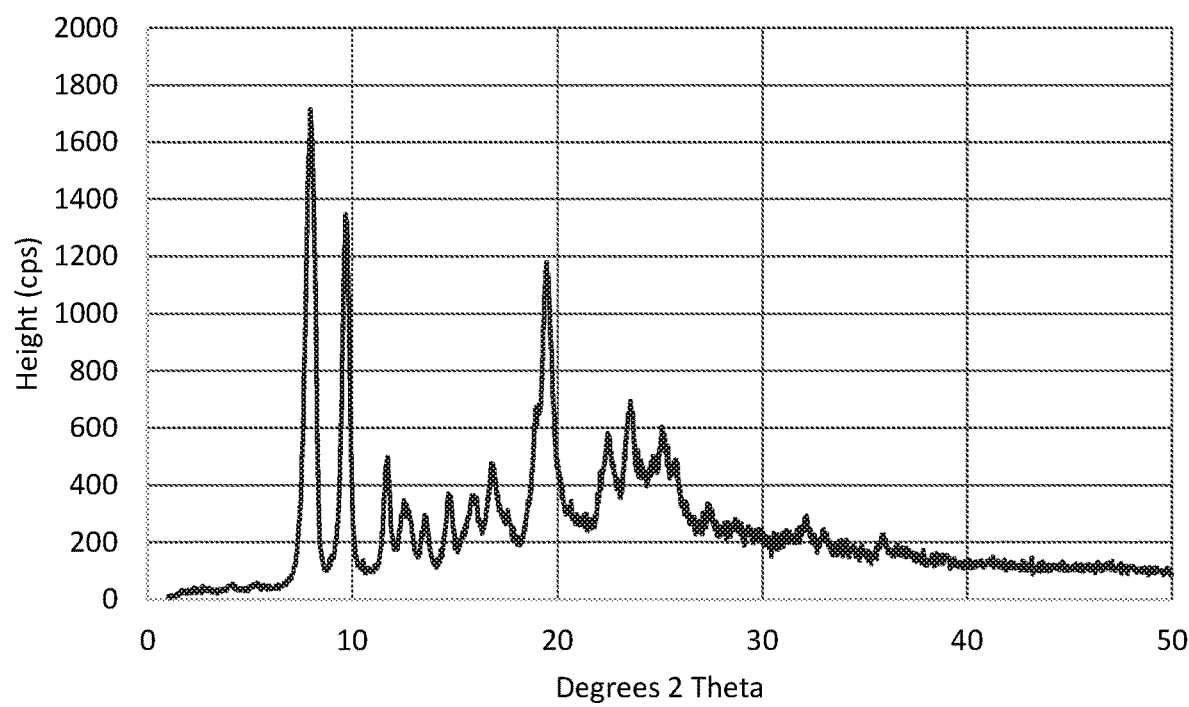
FIG. 4 provides an X-ray powder diffraction pattern for the presently disclosed Form II of crystalline nicotinic acid riboside triacetate (NARTA), the compound having formula (II), prepared according to an embodiment of the presently disclosed methods for the preparation of a crystalline form of nicotinic acid riboside triacetate (NARTA).

In other embodiments, the crystalline Form II of nicotinic acid riboside triacetate (NARTA, II) may be characterized by a powder X-ray diffraction pattern substantially as shown in FIG. 4. The crystalline Form II of nicotinic acid riboside triacetate (NARTA, II) may also or alternatively be characterized by a powder X-ray diffraction pattern peaks substantially as provided in Table 3, below, ±0.2 degrees two theta.

TABLE 3

| Peak No. | Pos. [°2Th.] | d-spacing [Å] | Heights [cts] | $I/I_{max}$ [%] |
|---|---|---|---|---|
| 1 | 8.0 | 10.998 | 1786 | 100 |
| 2 | 9.7 | 9.119 | 1412 | 79 |
| 3 | 11.7 | 7.57 | 389 | 22 |
| 4 | 12.6 | 7.035 | 202 | 11 |
| 5 | 13.6 | 6.531 | 136 | 8 |
| 6 | 14.7 | 6.02 | 196 | 11 |
| 7 | 15.9 | 5.563 | 161 | 9 |
| 8 | 16.8 | 5.268 | 232 | 13 |
| 9 | 19.0 | 4.67 | 413 | 23 |
| 10 | 19.4 | 4.572 | 928 | 52 |
| 11 | 22.4 | 3.96 | 216 | 12 |
| 12 | 23.5 | 3.783 | 314 | 18 |
| 13 | 25.1 | 3.54 | 199 | 11 |
| 14 | 32.2 | 2.781 | 77 | 4 |

X-ray diffraction patterns were collected with a Rigaku MiniFlex diffractometer using an incident beam of Cu radiation. A continuous scan was performed at 2.0 degrees two-theta per minute with a step width of 0.02 degrees two-theta.

Figure 5:
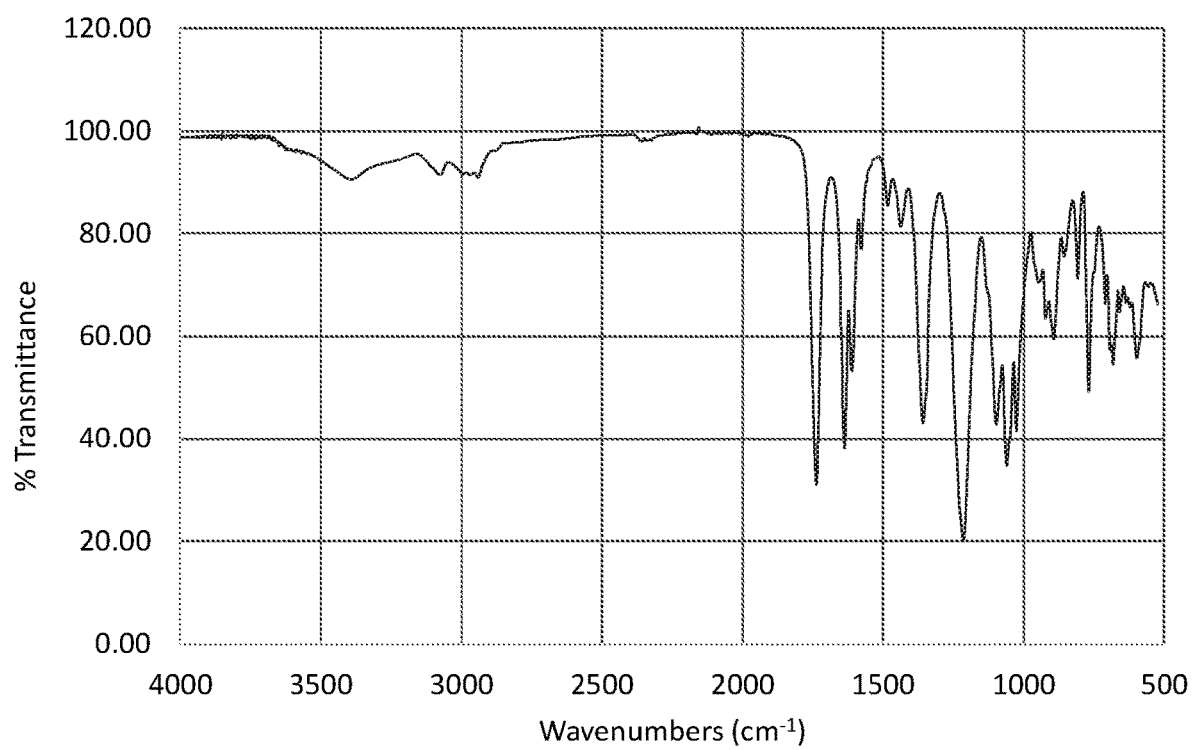
FIG. 5 provides a solid-state IR spectrum for the presently disclosed Form II of crystalline nicotinic acid riboside triacetate (NARTA), the compound having formula (II), prepared according to an embodiment of the presently disclosed methods for the preparation of a crystalline form of nicotinic acid riboside triacetate (NARTA).

The crystalline Form II of nicotinic acid riboside triacetate (NARTA, II) may also or alternatively be characterized by a solid-state IR spectrum having peaks at 599.3, 659.6, 683.2, 694.3, 710.7, 770.0, 809.0, 856.7, 893.4, 922.8, 948.8, 1638.7, and 1738.5 $cm^{-1}±0.2$ $cm^{-1}$. The crystalline Form II of nicotinic acid riboside triacetate (NARTA, II) may also or alternatively be characterized by a solid-state IR spectrum having peaks at 599.3, 659.6, 683.2, 694.3, 710.7, 770.0, 809.0, 856.7, 893.4, 922.8, 948.8, 1026.4, 1060.7, 1097.3, 1215.4, 1358.2, 1473.2, 1483.0, 1638.7, and 1738.5 $cm^{-1}±0.2$ $cm^{-1}$. The crystalline Form II of nicotinic acid riboside triacetate (NARTA, II) may also or alternatively by a solid-state IR spectrum having peaks at 599.3, 659.6, 683.2, 694.3, 710.7, 770.0, 809.0, 856.7, 893.4, 922.8, 948.8, 1026.4, 1060.7, 1097.3, 1215.4, 1358.2, 1473.2, 1483.0, 1579.0, 1612.2, 1638.7, and 1738.5 $cm^{-1}±0.2$ $cm^{-1}$. The crystalline Form II of nicotinic acid riboside triacetate (NARTA, II) may also or alternatively be characterized by a solid-state IR spectrum having peaks at 599.3, 659.6, 683.2, 694.3, 710.7, 770.0, 809.0, 856.7, 893.4, 922.8, 948.8, 1026.4, 1060.7, 1097.3, 1215.4, 1358.2, 1473.2, 1483.0, 1579.0, 1612.2, 1638.7, 1738.5, 2941.9, 2972.7, 2997.4, 3074.0, and 3392.71 $cm^{-1}±0.2$ $cm^{-1}$. In certain embodiments, the crystalline Form II of nicotinic acid riboside triacetate (NARTA, II) may also or alternatively be characterized by a solid-state IR spectrum as shown in FIG. 5. In further embodiments, the crystalline Form II of nicotinic acid riboside triacetate (NARTA, II) may also or alternatively be characterized by a solid-state IR spectrum having transmittance peaks substantially as provided in Table 4, below, ±0.2 $cm^{-1}$.

TABLE 4

| IR ($cm^{-1}$) |
|---|
| 3392.71 |
| 3074.03 |
| 2997.37 |
| 2972.70 |
| 2941.92 |
| 1738.54 |
| 1638.74 |
| 1612.23 |
| 1578.96 |
| 1483.02 |
| 1437.21 |
| 1358.15 |
| 1215.44 |
| 1097.32 |
| 1060.67 |
| 1026.44 |
| 948.82 |
| 922.79 |
| 893.38 |
| 856.74 |
| 809.01 |
| 769.95 |
| 710.65 |
| 694.26 |
| 683.17 |
| 659.55 |
| 599.28 |

IR spectra were acquired using a Thermo iS50 FT-IR spectrometer with diamond ATR accessory.

In another embodiment, crystalline Form II of nicotinic acid riboside triacetate (NARTA, II) is characterized by a DSC thermogram obtained using a heating rate of 10° C./min comprising an endothermic event with an onset temperature of 92.2° C.±2° C.

In yet another embodiment, crystalline Form II of nicotinic acid riboside triacetate (NARTA, II) is characterized by a DSC thermogram obtained using a heating rate of 10° C./min comprising an endothermic event with an onset temperature of 159.2° C.±2° C.

In yet another embodiment, crystalline Form II of nicotinic acid riboside triacetate (NARTA, II) is characterized by a DSC thermogram obtained using a heating rate of 10° C./min comprising an endothermic event with an onset temperature of 92.2° C.±2° C., an onset temperature of 159.2° C.±2° C., or both.

Figure 6:
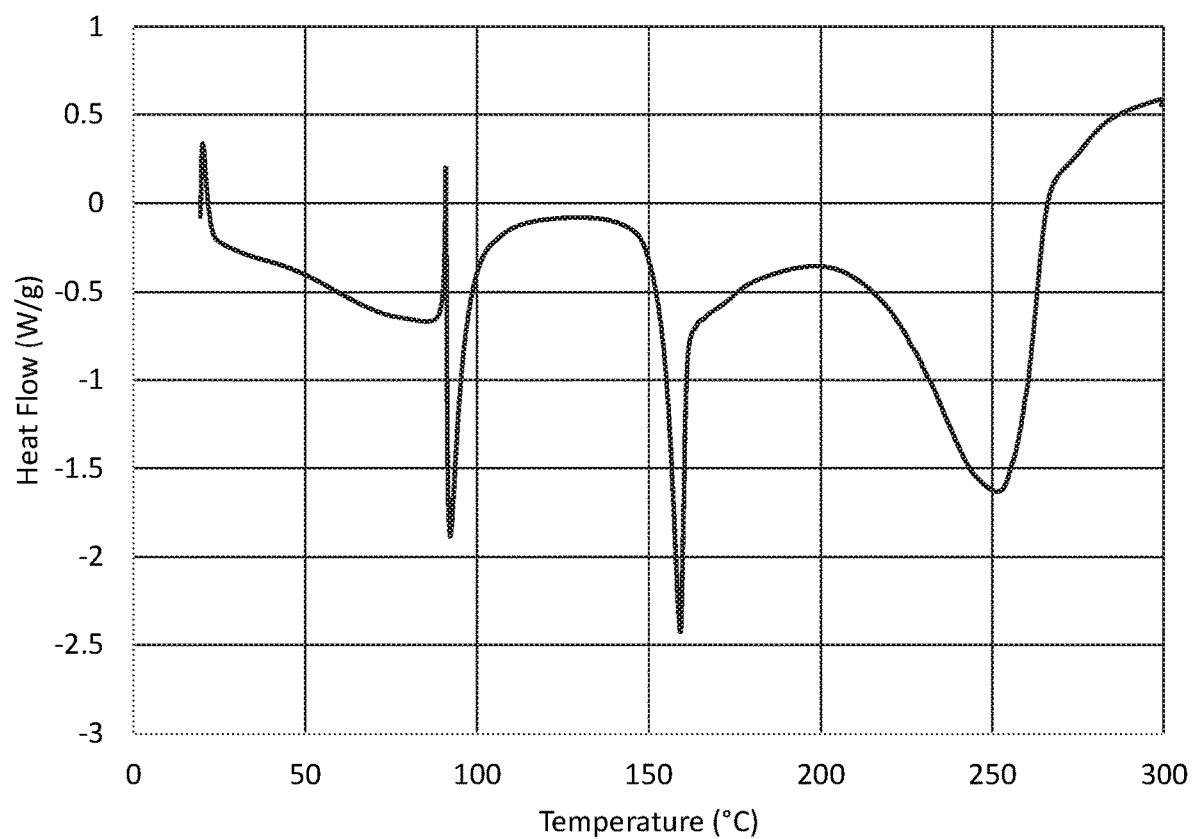
FIG. 6 provides a DSC thermogram for a sample of the presently disclosed Form II of crystalline nicotinic acid riboside triacetate (NARTA) that was heated at a rate of 10° C./min.

In yet another embodiment, crystalline Form II of nicotinic acid riboside triacetate (NARTA, II) may be characterized by a DSC thermogram substantially as shown in FIG. 6.

Differential Scanning Calorimetry was performed using a TA Instruments DSC Q20. The samples were scanned through the temperature range (20° C. to 300° C.) at 10° C./min (display exothermic up).

It is well known that the DSC onset and peak temperatures as well as energy values may vary due to, for example, the purity of the sample and sample size and due to instrumental parameters, especially the temperature scan rate. Hence the DSC data presented are not to be taken as absolute values. A person skilled in the art can set up instrumental parameters for a Differential Scanning Calorimeter so that data comparable to the data presented here can be collected according to standard methods, for example, those described in G. W. H. HÖHNE ET AL., DIFFERENTIAL SCANNING CALORIMETRY (Springer 1996).

The use of the terms "a," "an," "the," and similar referents in the context of describing the present invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise sindicated herein, and each separate value is incorporated into the specification as if it were individually recited herein. Use of the term "about" is intended to describe values either above or below the stated value in a range of approximately ±10%; in other embodiments, the values may range in value above or below the stated value in a range of approximately ±5%; in other embodiments, the values may range in value above or below the stated value in a range of approximately ±2%; in other embodiments, the values may range in value above or below the stated value in a range of approximately ±1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicated any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entireties. The present invention may be embodied in other specific forms without departing from the spirit or essential attributes thereof and, accordingly, reference should be made to the appended claims, rather than to the foregoing specification, as indicating the scope of the invention.

We claim:

1. A crystalline Form II of nicotinic acid riboside (NAR) according to formula (I):

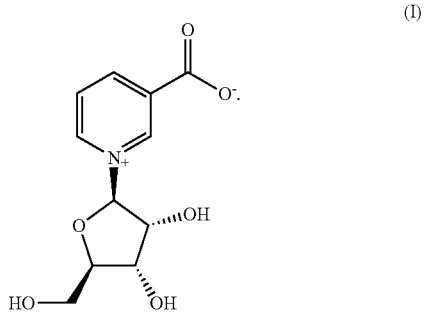

(I)

2. The crystalline Form II of claim 1 that is characterized by a powder X-ray diffraction pattern having peaks at 16.9, 17.7, and 26.6 degrees two theta±0.2 degrees two theta.

3. The crystalline Form II of claim 1 that is characterized by a powder X-ray diffraction pattern having peaks at 8.5, 15.8, 16.9, 17.7, and 26.6 degrees two theta±0.2 degrees two theta.

4. The crystalline Form II of claim 1 that is characterized by a powder X-ray diffraction pattern having peaks at 8.5, 13.9, 15.8, 16.9, 17.7, 21.7, 22.0, 26.1, 26.6, and 27.9 degrees two theta±0.2 degrees two theta.

5. The crystalline Form II of claim 1 that is characterized by a powder X-ray diffraction pattern having peaks substantially as shown in FIG. 1.

6. The crystalline Form II of claim 1 that is characterized by a powder X-ray diffraction pattern having peaks substantially as provided in Table 1±0.2 degrees two theta.

7. The crystalline Form II of claim 1 that is characterized by an IR spectrum having peaks at 754.0, 775.3, 867.8, 923.8, and 1641.2 cm$^{-1}$±0.2 cm$^{-1}$.

8. The crystalline Form II of claim 1 that is characterized by an IR spectrum having peaks at 754.0, 775.3, 867.8, 923.8, 1054.9, 1087.7, 1114.7, 1135.9, 1184.1, and 1641.2 cm$^{-1}$±0.2 cm$^{-1}$.

9. The crystalline Form II of claim 1 that is characterized by an IR spectrum having peaks at 754.0, 775.3, 867.8, 923.8, 1054.9, 1087.7, 1114.7, 1135.9, 1184.1, 1309.5, 1322.9, 1359.6, and 1641.2 cm$^{-1}$±0.2 cm$^{-1}$.

10. The crystalline Form II of claim 1 that is characterized by an IR spectrum having peaks at 754.0, 775.3, 867.8, 923.8, 1054.9, 1087.7, 1114.7, 1135.9, 1184.1, 1309.5, 1322.9, 1359.6, 1579.4, 1612.2, 1641.2, 3043.2, and 3259.2 cm$^{-1}$±0.2 cm$^{-1}$.

11. The crystalline Form II of claim 1 that is characterized by an IR spectrum substantially as shown in FIG. 2.

12. The crystalline Form II of claim 1 that is characterized by a DSC thermogram substantially as shown in FIG. 3.

13. The crystalline Form II of claim 1 that is characterized by a DSC thermogram obtained using a heating rate of 10° C./min comprising an endothermic event with an onset temperature of 153.0° C.±2° C.

14. The crystalline Form II of claim 1 that is characterized by a DSC thermogram obtained using a heating rate of 10° C./min comprising an endothermic event with a peak temperature of 155.9° C.±2° C.

15. The crystalline Form II of claim 1 that is characterized by a DSC thermogram obtained using a heating rate of 10° C./min comprising an endothermic event with an onset temperature of 153.0° C.±2° C. and a peak temperature of 155.9° C.±2° C.

16. The crystalline Form II of claim 1 that is prepared by a method comprising the steps of:
    (a) adding a volume of hexafluoroisopropanol to a mass of nicotinic acid riboside;
    (b) dissolving the mass of nicotinic acid riboside in the volume of hexafluoroisopropanol so as to produce a solution of nicotinic acid riboside in hexafluoroisopropanol;
    (c) adding the solution of nicotinic acid riboside in hexafluoroisopropanol to an open vessel;
    (d) placing the open vessel containing the solution of nicotinic acid riboside in hexafluoroisopropanol inside a larger vessel containing a volume of ethyl acetate that is approximately equal to the volume of the solution of nicotinic acid riboside in hexafluoroisopropanol;
    (e) sealing the larger vessel;
    (f) maintaining the solution of nicotinic acid riboside in hexafluoroisopropanol at ambient temperature so as to crystallize the crystalline Form II of nicotinic acid riboside;
    (g) unsealing the larger vessel; and
    (h) isolating the crystalline Form II of nicotinic acid riboside.

17. A crystalline Form II of nicotinic acid riboside triacetate (NARTA) according to formula (II):

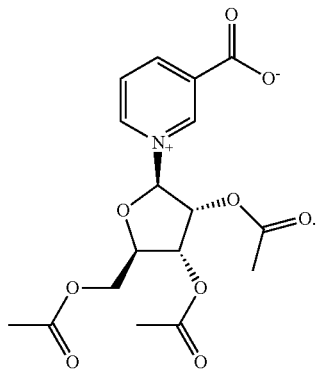

(II)

18. The crystalline Form II of claim 17 that is characterized by a powder X-ray diffraction pattern having peaks at 8.0, 9.7, and 19.4 degrees two theta±0.2 degrees two theta.

19. The crystalline Form II of claim 17 that is characterized by a powder X-ray diffraction pattern having peaks at 8.0, 9.7, 11.7, 19.0, 19.4, and 23.5 degrees two theta±0.2 degrees two theta.

20. The crystalline Form II of claim 17 that is characterized by a powder X-ray diffraction pattern having peaks at 8.0, 9.7, 11.7, 12.6, 14.7, 16.8, 19.0, 19.4, 22.4, 23.5, and 25.1 degrees two theta±0.2 degrees two theta.

21. The crystalline Form II of claim 17 that is characterized by a powder X-ray diffraction pattern having peaks substantially as shown in FIG. 4.

22. The crystalline Form II of claim 17 that is characterized by a powder X-ray diffraction pattern having peaks substantially as provided in Table 3±0.2 degrees two theta.

23. The crystalline Form II of claim 17 that is characterized by an IR spectrum having peaks at 599.3, 659.6, 683.2, 694.3, 710.7, 770.0, 809.0, 856.7, 893.4, 922.8, 948.8, 1638.7, and 1738.5 cm$^{-1}$±0.2 cm$^{-1}$.

24. The crystalline Form II of claim 17 that is characterized by an IR spectrum having peaks at 599.3, 659.6, 683.2, 694.3, 710.7, 770.0, 809.0, 856.7, 893.4, 922.8, 948.8, 1026.4, 1060.7, 1097.3, 1215.4, 1358.2, 1473.2, 1483.0, 1638.7, and 1738.5 cm$^{-1}$±0.2 cm$^{-1}$.

25. The crystalline Form II of claim 17 that is characterized by an IR spectrum having peaks at 599.3, 659.6, 683.2, 694.3, 710.7, 770.0, 809.0, 856.7, 893.4, 922.8, 948.8, 1026.4, 1060.7, 1097.3, 1215.4, 1358.2, 1473.2, 1483.0, 1579.0, 1612.2, 1638.7, and 1738.5 cm$^{-1}$±0.2 cm$^{-1}$.

26. The crystalline Form II of claim 17 that is characterized by an IR spectrum having peaks substantially as provided in Table 4±0.2 cm$^{-1}$.

27. The crystalline Form II of claim 17 that is characterized by an IR spectrum substantially as shown in FIG. 5.

28. The crystalline Form II of claim 17 that is characterized by a DSC thermogram substantially as shown in FIG. 6.

29. The crystalline Form II of claim 17 that is characterized by a DSC thermogram obtained using a heating rate of 10° C./min comprising an endothermic event with an onset temperature of 92.2° C.±2° C.

30. The crystalline Form II of claim 17 that is characterized by a DSC thermogram obtained using a heating rate of 10° C./min comprising an endothermic event with an onset temperature of 159.2° C.±2° C.

31. The crystalline Form II of claim 17 that is characterized by a DSC thermogram obtained using a heating rate of 10° C./min comprising endothermic events with onset temperatures at 92.2° C.±2° C. and 159.2° C.±2° C.

32. The crystalline Form II of claim 17 that is prepared by a method comprising the steps of:
    (a) adding a volume of ethanol to a mass of nicotinic acid riboside triacetate;
    (b) dissolving the mass of nicotinic acid riboside triacetate in the volume of ethanol at approximately 50° C. so as to produce a solution of nicotinic acid riboside triacetate in ethanol;
    (c) cooling the solution of nicotinic acid riboside triacetate in ethanol at −20° C. so as to crystallize the crystalline Form II of nicotinic acid riboside triacetate; and
    (d) isolating the crystalline Form II of nicotinic acid riboside triacetate.

* * * * *